United States Patent
Gross et al.

(10) Patent No.: US 11,975,203 B1
(45) Date of Patent: May 7, 2024

(54) PROSTHETIC AORTIC VALVE PACING SYSTEMS

(71) Applicants: Yossi Gross, Moshav Mazor (IL); Navot Rabban, Ramat Gan (IL); Meni Iamberger, Kfar Saba (IL); Aharon Daffan, Jerusalem (IL)

(72) Inventors: Yossi Gross, Moshav Mazor (IL); Navot Rabban, Ramat Gan (IL); Meni Iamberger, Kfar Saba (IL); Aharon Daffan, Jerusalem (IL)

(73) Assignee: E-VALVE SYSTEMS LTD., Herzliya (IL)

( * ) Notice: Subject to any disclaimer, the term of this patent is extended or adjusted under 35 U.S.C. 154(b) by 0 days.

(21) Appl. No.: 18/452,216

(22) Filed: Aug. 18, 2023

(51) Int. Cl.
| A61N 1/375 | (2006.01) |
| A61F 2/24 | (2006.01) |
| A61N 1/05 | (2006.01) |
| A61N 1/362 | (2006.01) |
| A61N 1/372 | (2006.01) |

(52) U.S. Cl.
CPC .......... *A61N 1/3629* (2017.08); *A61F 2/2418* (2013.01); *A61N 1/057* (2013.01); *A61N 1/37229* (2013.01); *A61N 1/37512* (2017.08); *A61N 1/37518* (2017.08)

(58) Field of Classification Search
CPC .. A61N 1/3629; A61N 1/057; A61N 1/37229; A61N 1/37512; A61N 1/37518; A61F 2/2418
See application file for complete search history.

(56) References Cited

U.S. PATENT DOCUMENTS

| 3,745,995 A | 7/1973 | Kraus |
| 4,256,094 A | 3/1981 | Kapp et al. |
| 4,979,955 A | 12/1990 | Smith |

(Continued)

FOREIGN PATENT DOCUMENTS

| CN | 110534284 B | 5/2022 |
| EP | 3508113 | 7/2019 |

(Continued)

OTHER PUBLICATIONS

A Notice of Allowance issued in U.S. Appl. No. 17/328,588, dated Mar. 10, 2022.

(Continued)

*Primary Examiner* — Eugene T Wu
(74) *Attorney, Agent, or Firm* — Sughrue Mion, PLLC

(57) ABSTRACT

A prosthetic aortic valve is provided including a frame including interconnected stent struts arranged so as to define interconnected stent cells. A plurality of prosthetic leaflets are coupled to the frame so as to allow blood flow in a downstream direction and inhibit blood flow in an upstream direction when the prosthetic aortic valve is in an expanded deployment configuration. Circuitry is mechanically coupled to the frame. An electrode is mechanically coupled to the frame. A printed circuit board (PCB) is shaped so as to define an elongate portion. An electrical lead electrically couples the electrode to the circuitry, and is integral with the elongate portion of the PCB. The elongate portion of the PCB is mechanically coupled to some of the interconnected stent struts of the frame. Other embodiments are also described.

22 Claims, 16 Drawing Sheets

(56) References Cited

U.S. PATENT DOCUMENTS

| | | | |
|---|---|---|---|
| 5,487,760 A | 1/1996 | Villafana | |
| 6,030,335 A | 2/2000 | Franchi | |
| 6,030,336 A | 2/2000 | Franchi | |
| 6,050,932 A | 4/2000 | Franchi | |
| 7,643,879 B2 | 1/2010 | Shuros et al. | |
| 7,914,569 B2 | 3/2011 | Nguyen et al. | |
| 8,092,365 B2 | 1/2012 | Rinderknecht et al. | |
| 8,239,023 B2 | 8/2012 | Shuros et al. | |
| 8,471,562 B2 | 6/2013 | Knizhnik | |
| 8,628,525 B2 | 1/2014 | Wirtz et al. | |
| 8,704,721 B2 | 4/2014 | Ferrer Herrera et al. | |
| 9,005,106 B2 | 4/2015 | Gross et al. | |
| 9,326,854 B2 | 5/2016 | Casley et al. | |
| 9,526,637 B2 * | 12/2016 | Dagan | A61B 5/0215 |
| 9,662,211 B2 | 5/2017 | Hodson et al. | |
| 9,737,264 B2 | 8/2017 | Braido et al. | |
| 9,808,201 B2 | 11/2017 | Braido et al. | |
| 10,543,083 B2 | 1/2020 | Gross | |
| 10,758,725 B2 | 9/2020 | Daniels et al. | |
| 10,835,750 B2 | 11/2020 | Gross | |
| 11,013,597 B2 | 5/2021 | Gross | |
| 11,065,451 B1 | 7/2021 | Gross | |
| 11,096,605 B2 | 8/2021 | Wald et al. | |
| 2003/0032853 A1 | 2/2003 | Korakianitis et al. | |
| 2004/0024285 A1 | 2/2004 | Muckter | |
| 2004/0097784 A1 | 5/2004 | Peters et al. | |
| 2004/0111006 A1 | 6/2004 | Alferness et al. | |
| 2005/0049696 A1 | 3/2005 | Siess et al. | |
| 2006/0178707 A1 | 8/2006 | Thomas et al. | |
| 2006/0206170 A1 | 9/2006 | Denker et al. | |
| 2006/0213682 A1 | 9/2006 | Moon et al. | |
| 2008/0077016 A1 | 3/2008 | Sparks et al. | |
| 2010/0197994 A1 | 8/2010 | Mehmanesh | |
| 2011/0071351 A1 | 3/2011 | Sperling | |
| 2011/0137370 A1 | 6/2011 | Gross et al. | |
| 2011/0196482 A1 | 8/2011 | Forsell | |
| 2012/0197350 A1 | 8/2012 | Roberts et al. | |
| 2012/0245678 A1 | 9/2012 | Solem | |
| 2012/0265296 A1 | 10/2012 | McNamara et al. | |
| 2012/0296382 A1 | 11/2012 | Shuros et al. | |
| 2013/0138205 A1 | 5/2013 | Kushwaha et al. | |
| 2013/0297009 A1 | 11/2013 | Chalekian et al. | |
| 2014/0066895 A1 | 3/2014 | Kipperman | |
| 2014/0081154 A1 | 3/2014 | Toth | |
| 2014/0180391 A1 | 6/2014 | Dagan et al. | |
| 2014/0275720 A1 | 9/2014 | Ferrari | |
| 2015/0128684 A1 | 5/2015 | Hodson et al. | |
| 2016/0045165 A1 | 2/2016 | Braido et al. | |
| 2016/0045316 A1 | 2/2016 | Braido et al. | |
| 2016/0144091 A1 | 5/2016 | Breedon et al. | |
| 2016/0278951 A1 | 9/2016 | Dagan et al. | |
| 2017/0100527 A1 | 4/2017 | Schwammenthal et al. | |
| 2017/0258585 A1 | 9/2017 | Marquez et al. | |
| 2017/0266433 A1 | 9/2017 | Daniels et al. | |
| 2019/0076588 A1 | 3/2019 | Ochsner et al. | |
| 2019/0209302 A1 * | 7/2019 | Gross | A61B 5/287 |
| 2020/0139121 A1 | 5/2020 | Gross | |
| 2020/0261224 A1 | 8/2020 | Gross | |
| 2020/0282204 A1 | 9/2020 | Capek et al. | |
| 2020/0324033 A1 | 10/2020 | Agah et al. | |
| 2021/0283397 A1 * | 9/2021 | Gross | A61B 5/318 |

FOREIGN PATENT DOCUMENTS

| | | |
|---|---|---|
| EP | 3 785 758 A1 | 3/2021 |
| FR | 3034650 | 10/2016 |
| WO | 2013/035092 | 3/2013 |
| WO | 2013/111137 A1 | 8/2013 |
| WO | 2014/043235 | 3/2014 |
| WO | 2016/157183 | 10/2016 |
| WO | 2020/210490 A1 | 10/2020 |
| WO | 2021/140507 A1 | 7/2021 |
| WO | 2021/224904 A1 | 11/2021 |
| WO | 2022/149130 A1 | 7/2022 |

OTHER PUBLICATIONS

An International Search Report (ISR) and Written Opinion issued in PCT/IL2021/050017, dated Jun. 9, 2021.
A Corrected International Search Report (ISR) and Written Opinion issued in PCT/IL2021/050016, dated Sep. 20, 2021.
An International Search Report (ISR) and Written Opinion issued in PCT/IL2022/050019, dated May 6, 2022.
A Communication under Art 94(3) EPC issued in European Appl. No. EP19150581.7, dated Aug. 30, 2022.
Zhongyu Dai, et al., "Selective Omnidirectional Magnetic Resonant Coupling Wireless Power Transfer With Multiple-Receiver System", IEEE Access, Feb. 2018, vol. 6, pp. 19287-19294.
Ding Han, et al., "A Three-Dimensional Orthogonal Receiving Coil for In Vivo Microrobot Wireless Power Transmission Systems", Energies, 2022, vol. 15, No. 6321, pp. 1-13.
Harwin, "Hi-Rel Flex Circuit Assemblies," Product Brochure, Jul. 11, 2022, CP054/07112022, pp. 1-13.
Michael Traskos, "Should Polymide Insulated Wire be Trusted?", Lectromec, Sep. 25, 2018, pp. 1-7.
"Pacing at the Bundle of His," Medtronic, Inc., Minneapolis, MN, USA (Oct. 2017).
"Medtronic Evolut™ PRO System brochure," Medtronic, Inc., Minneapolis, MN, USA (Mar. 2017).
"Medtronic CoreValve™ System Instructions for Use," Medtronic, Inc., Minneapolis, MN, USA (2014).
An Office Action dated Apr. 11, 2019, which issued during the prosecution of U.S. Appl. No. 15/864,661.
European Search Report dated May 17, 2019 which issued during the prosecution of Applicant's European App No. 19150581.7.
Jobanputra Y et al., "Rapid Ventricular Pacing During Transcatheter Valve Procedures Using an Internal Device and Programmer: A Demonstration of Feasibility," JACC Mar. 20, 2018, vol. 71, Issue 11, p. 1381.
An Office Action dated Apr. 27, 2020, which issued during the prosecution of U.S. Appl. No. 16/734,798.
Notice of Allowance dated Aug. 3, 2020, which issued during the prosecution of U.S. Appl. No. 16/734,798.
Notice of Allowance dated Jan. 25, 2021, which issued during the prosecution of U.S. Appl. No. 16/868,121.
An Office Action dated Nov. 23, 2020, which issued during the prosecution of U.S. Appl. No. 16/868,121.
Notice of Allowance dated Sep. 26, 2019, which issued during the prosecution of U.S. Appl. No. 15/864,661.
Notice of Allowance dated Mar. 22, 2021, which issued during the prosecution of U.S. Appl. No. 17/142,729.

* cited by examiner

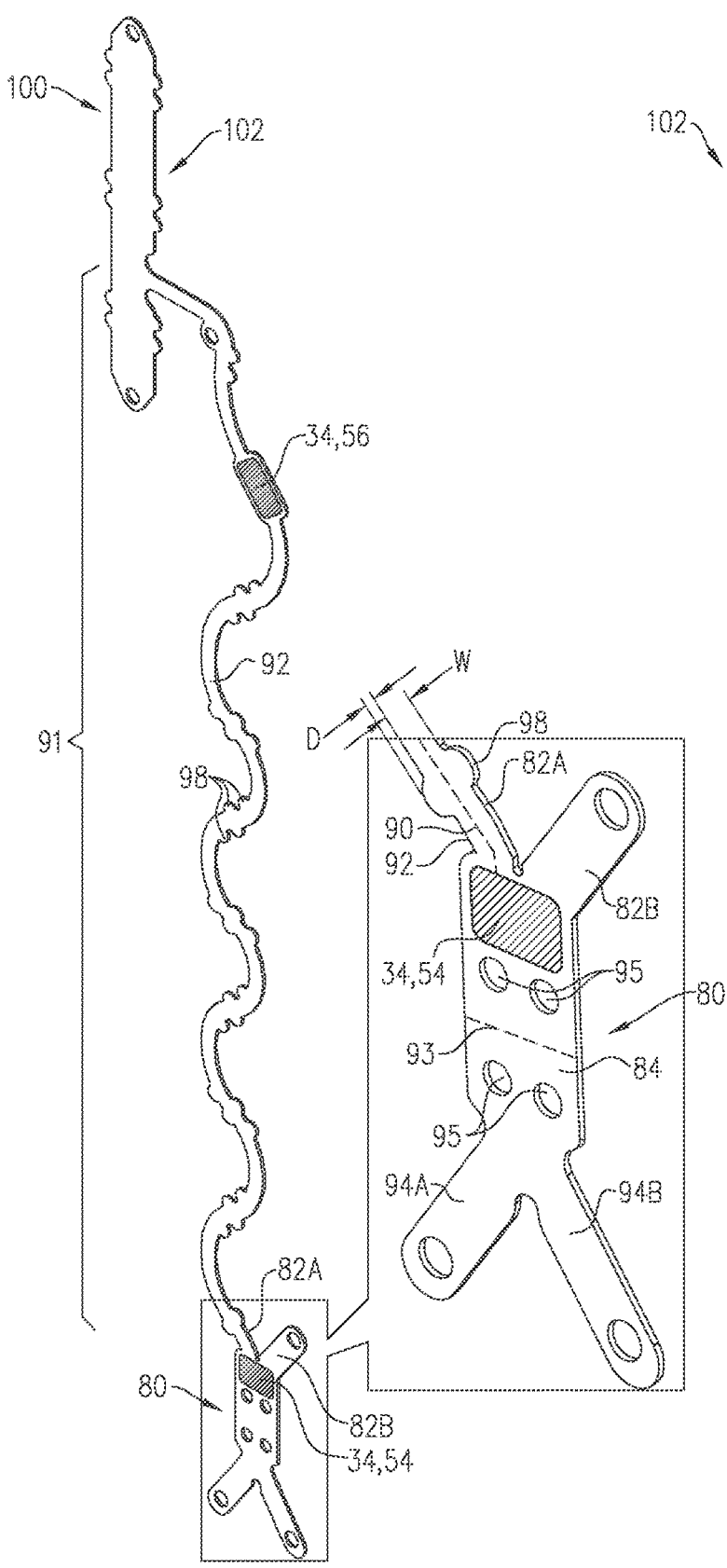
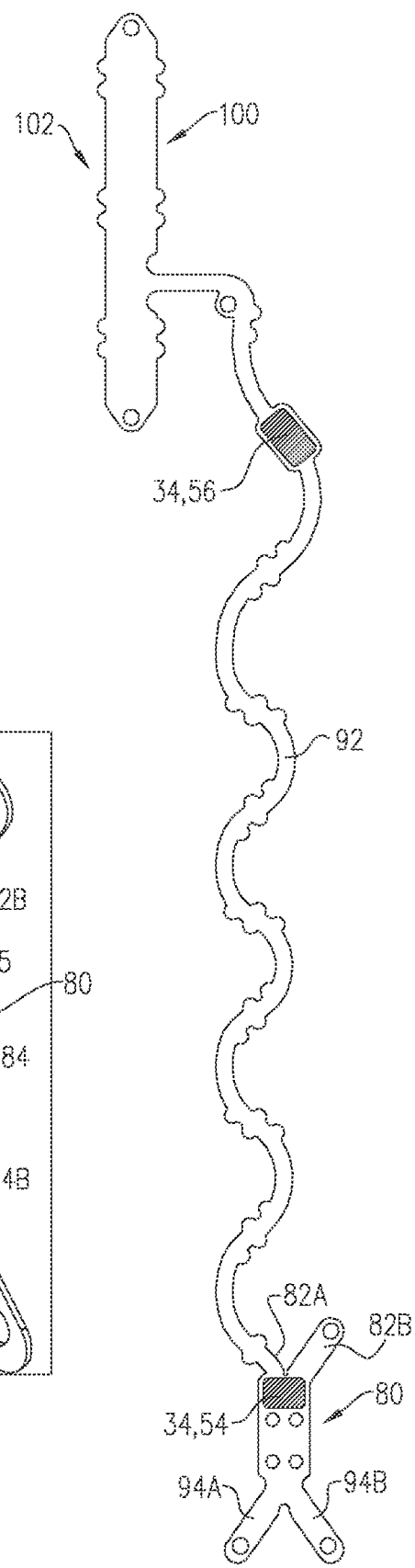
FIG. 3A
FIG. 3B

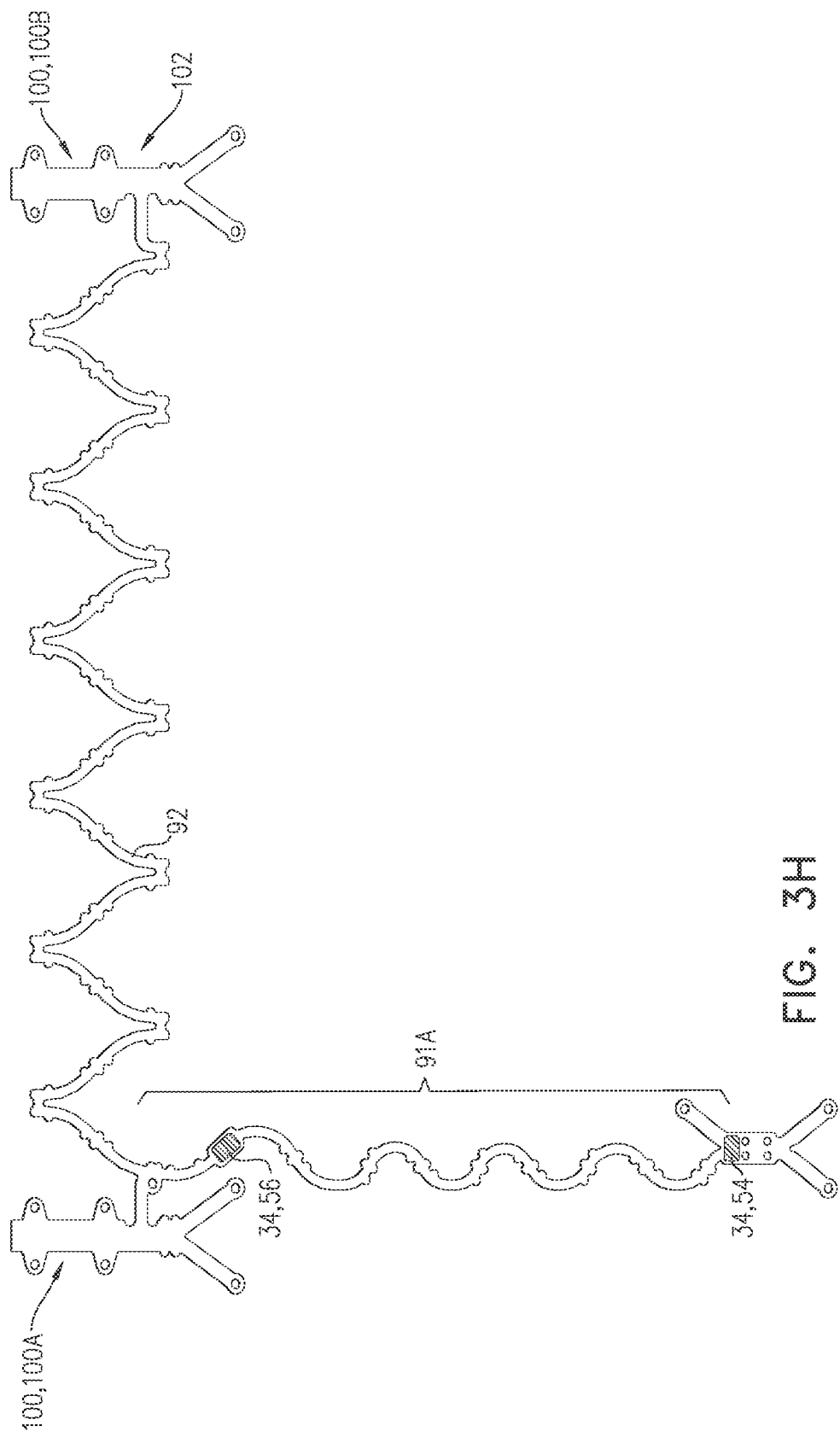

PROSTHETIC AORTIC VALVE PACING SYSTEMS

CROSS-REFERENCE TO RELATED APPLICATIONS

The present application is related to U.S. application Ser. No. 18/452,229, filed Aug. 18, 2023, entitled, "Prosthetic aortic valve pacing systems," which is incorporated herein by reference.

FIELD OF THE APPLICATION

The present invention relates generally to surgical implants and systems, and specifically to prosthetic aortic valves and systems.

BACKGROUND OF THE APPLICATION

Aortic heart valve replacement may be necessary to treat valve regurgitation or stenotic calcification of the leaflets. In percutaneous transluminal delivery techniques, a prosthetic aortic valve is compressed for delivery in a catheter and advanced through the descending aorta to the heart, where the prosthetic valve is deployed in the aortic valve annulus. New-onset cardiac conduction disturbances are common after transcatheter aortic valve replacement (TAVR). The most common complication is left bundle branch block (LBBB).

PCT Publication WO 2022/149130 to Gross, which is incorporated herein by reference, inter alia describes a prosthetic aortic valve, which is configured to be delivered to a native aortic valve of a patient in a constrained delivery configuration within a delivery sheath. The prosthetic aortic valve includes a frame, which includes interconnected stent struts arranged so as to define interconnected stent cells; a plurality of prosthetic leaflets coupled to the frame; a cathode and an anode, which are mechanically coupled to the frame; and a prosthetic-valve coil, which is in non-wireless electrical communication with the cathode and the anode, and is coupled to a plurality of the stent struts, running along the stent struts so as to surround a plurality of the stent cells when the prosthetic aortic valve is in an expanded fully-deployed configuration upon release from the delivery sheath.

US Patent Application Publication 2017/0258585 to Marquez et al. describes sensor-integrated prosthetic valves that can comprise a variety of features, including a plurality of valve leaflets, a frame assembly configured to support the plurality of valve leaflets and define a plurality of commissure supports terminating at an outflow end of the prosthetic valve, a sensor device associated with the frame assembly and configured to generate a sensor signal, for example, a sensor signal indicating deflection of one or more of the plurality of commissure supports, and a transmitter assembly configured to receive the sensor signal from the sensor device and wirelessly transmit a transmission signal that is based at least in part on the sensor signal.

U.S. Pat. No. 9,326,854 to Casley et al. describes medical device delivery assemblies. The assembly may include a catheter-based delivery system. The assembly may include a pacing element to pace a patient's heart before, during, or after a procedure. The pacing element may be a detachable, implanting pacing element. The pacing element may be an implantable pacemaker and the implantable pacemaker may be disposed on a catheter-based delivery system. The assembly may include a prosthetic heart valve with one or more pacing elements on it. The pacing element may include a pacing strip or strips. These strips may be conductive or insulative. These strips may prevent, treat, or correct abnormal electrical communication in a heart.

SUMMARY OF THE APPLICATION

Some embodiments of the present invention provide a prosthetic aortic valve, which is configured to be implanted in a native aortic valve of a patient, and which comprises a plurality of prosthetic leaflets, a frame, and one or more electrodes, including a cathode and an anode, mechanically coupled to the frame. The prosthetic aortic valve further comprises a prosthetic-valve coil, which is in non-wireless electrical communication with the cathode and the anode.

For some applications, the prosthetic aortic valve further comprises circuitry, which is configured to apply pacing to the heart using the one or more electrodes. For example, the pacing may be applied temporarily for up to several weeks after implantation of the prosthetic aortic valve, typically using an external control unit to continuously provide power, or applied longer-term, in which case the prosthetic aortic valve may further comprise an energy storage module, e.g., comprising a battery, which may be periodically charged using the external control unit. Further alternatively or additionally, for some applications, the circuitry is configured to apply rapid pacing during an invasive structural heart procedure, such as an implantation procedure, such as a transcatheter aortic valve replacement (TAVR)-in-TAVR procedure in which the first TAVR comprises the prosthetic aortic valve.

There is therefore provided, in accordance with an application of the present invention, a prosthetic aortic valve, which is configured to be delivered to a native aortic valve of a patient in a constrained delivery configuration, and which includes:

a frame, which defines a central longitudinal axis when the prosthetic aortic valve is in an expanded deployment configuration, and which includes interconnected stent struts arranged so as to define interconnected stent cells, wherein upstream ones of the stent cells are located in an upstream half of the frame and define respective upstream peaks;

a plurality of prosthetic leaflets coupled to the frame so as to allow blood flow in a downstream direction and inhibit blood flow in an upstream direction;

an electrode, which is disposed at or near an upstream peak of one of the upstream stent cells, wherein first and second upstream stent struts of the one of the upstream stent cells are joined at the upstream peak; and coupling material, which is shaped so as to define:
(a) a first strip that is mechanically coupled to the first upstream stent strut,
(b) a second strip that is mechanically coupled to the second upstream stent strut, and
(c) a junction, which couples together the first and the second strips,
such that the first and the second strips together couple the electrode to the frame at or near the upstream peak.

For some applications, the upstream ones of the stent cells are upstream-most ones of the stent cells, and the one of the upstream stent cells is one of the upstream-most stent cells.

For some applications, the first and the second strips are mechanically coupled to the first and the second upstream stent struts, respectively, by stitching.

For some applications, the junction of the coupling material is mechanically coupled to the frame at or near the upstream peak.

For some applications, the first strip has length equal to at least 50% of a length of the first upstream stent strut.

For some applications, the length of the first strip is greater than the length of the first upstream stent strut.

For some applications, the second strip has length equal to at least 50% of a length of the second upstream stent strut.

For some applications, the length of the second strip is no more than 100% of the length of the second upstream stent strut.

For some applications:
the one of the upstream stent cells is a first one of the upstream stent cells,
the first one of the upstream stent cells is joined at a cell junction to a circumferentially-adjacent second one of the upstream stent cells, and
the second strip is mechanically coupled to the cell junction.

For some applications, the second strip is mechanically coupled to the cell junction by stitching.

For some applications:
the prosthetic aortic valve further includes an electrical lead, which is electrically coupled to the electrode, and
the first strip is mechanically coupled to at least a portion of the electrical lead.

For some applications:
the first strip includes electrical insulation, and
the first strip electrically insulates the at least a portion of the electrical lead.

For some applications, the first strip includes an elongate portion of a printed circuit board (PCB) with which the electrical lead is integral.

For some applications, the prosthetic aortic valve further includes circuitry, which is electrically coupled to the electrode by the electrical lead.

For some applications:
the first and the second strips are outer first and second strips, which are mechanically coupled to radially outer sides of the first and the second upstream stent struts, respectively,
the coupling material is shaped so as to further define:
  (a) an inner first strip that is mechanically coupled to a radially inner side of the first upstream stent strut, and
  (b) an inner second strip that is mechanically coupled to a radially inner side of the second upstream stent strut,
the junction of the coupling material couples together the outer first strip, the outer second strip, the inner first strip, and the inner second strip, and
the outer first strip, the outer second strip, the inner first strip, and the inner second strip together couple the electrode to the frame at or near the upstream peak.

For some applications, the junction of the coupling material is folded over the upstream peak.

For some applications, the folded junction is mechanically coupled to the frame at or near the upstream peak.

There is further provided, in accordance with an application of the present invention, a prosthetic aortic valve, which is configured to be delivered to a native aortic valve of a patient in a constrained delivery configuration, and which includes:
a frame, which defines a central longitudinal axis when the prosthetic aortic valve is in an expanded deployment configuration, and which includes interconnected stent struts arranged so as to define interconnected stent cells, including a first stent cell shaped so as to define:
  two peaks, consisting of an upstream peak and a downstream peak,
  two lateral nodes, consisting of a left lateral node and a right lateral node,
  two left stent struts, consisting of (a) an upstream left stent strut joined with the upstream peak and the left lateral node, and (b) a downstream left stent strut joined with the downstream peak and the left lateral node, and
  two right stent struts, consisting of (a) an upstream right stent strut joined with the upstream peak and the right lateral node, and (b) a downstream right stent strut joined with the downstream peak and the right lateral node;
a plurality of prosthetic leaflets coupled to the frame so as to allow blood flow in a downstream direction and inhibit blood flow in an upstream direction;
an electronic component, which is disposed at or near one of the peaks; and
coupling material, which is shaped so as to define:
  (a) a first strip that is mechanically coupled to at least one of the left stent struts,
  (b) a second strip that is mechanically coupled to at least one of the right stent struts, and
  (c) a junction, which couples together the first and the second strips,
  such that the first and the second strips together couple the electronic component to the frame at or near the one of the peaks.

For some applications, the prosthetic aortic valve includes circuitry, which includes the electronic component, and which is disposed at or near the one of the peaks.

For some applications, the electronic component includes an electrode.

For some applications, the electronic component includes an energy storage module.

For some applications, the first and the second strips together couple the electronic component to the frame at least partially outside the first stent cell at or near the one of the peaks.

For some applications, the first and the second strips are mechanically coupled to the at least one of the left stent struts and the at least one of the right stent struts, respectively, by stitching.

For some applications, the junction of the coupling material is mechanically coupled to the frame at or near the one of the peaks.

For some applications, the first strip has length equal to at least 50% of a length of the at least one of the left stent struts.

For some applications, the length of the first strip is greater than the length of the at least one of the left stent struts.

For some applications, the second strip has length equal to at least 50% of a length of the at least one of the right stent struts.

For some applications, the length of the second strip is greater than the length of the at least one of the right stent struts.

For some applications, the first strip is mechanically coupled to the left lateral node.

For some applications, the first strip is mechanically coupled to the left lateral node by stitching.

For some applications, the second strip is mechanically coupled to the right lateral node.

For some applications, the second strip is mechanically coupled to the right lateral node by stitching.

For some applications:
the prosthetic aortic valve further includes an electrical lead, which is electrically coupled to the electronic component, and
the first strip is mechanically coupled to at least a portion of the electrical lead.

For some applications:
the first strip includes electrical insulation, and
the first strip electrically insulates the at least a portion of the electrical lead.

For some applications, the first strip includes an elongate portion of a printed circuit board (PCB) with which the electrical lead is integral.

There is still further provided, in accordance with an application of the present invention, a prosthetic aortic valve, which is configured to be delivered to a native aortic valve of a patient in a constrained delivery configuration, and which includes:
a frame, which defines a central longitudinal axis when the prosthetic aortic valve is in the constrained delivery configuration, and which includes interconnected stent struts arranged so as to define interconnected stent cells;
a plurality of prosthetic leaflets coupled to the frame so as to allow blood flow in a downstream direction and inhibit blood flow in an upstream direction when the prosthetic aortic valve is in an expanded deployment configuration;
circuitry, which is mechanically coupled to the frame;
an electrode, which is mechanically coupled to the frame;
a printed circuit board (PCB), which is shaped so as to define an elongate portion; and
an electrical lead, which electrically couples the electrode to the circuitry, and which is integral with the elongate portion of the PCB, and
wherein the elongate portion of the PCB is mechanically coupled to some of the interconnected stent struts of the frame.

For some applications, the elongate portion of the PCB has an undulating shape that generally runs along the interconnected stent struts.

For some applications, the circuitry is mechanically coupled to the frame downstream of the prosthetic leaflets, and the electrode is mechanically coupled to the frame upstream of the prosthetic leaflets.

For some applications, the stent struts and the elongate portion of the PCB are rectangular in cross section taken perpendicular to respective longitudinal axes of the stent struts and the elongate portion.

For some applications, a ratio of a thickness of the stent struts to a thickness of the electrical lead is 5-15.

For some applications, a ratio of a thickness of the stent struts to a thickness of the elongate portion of the PCB is 2-5.

For some applications, the circuitry includes (a) a circuitry portion of the PCB distinct from the elongate portion of the PCB, (b) tracks of the PCB, (c) conductive pads of the PCB, and (d) electronic components coupled to the PCB.

For some applications:
the circuitry portion of the PCB is a first circuitry portion of the PCB, and
the PCB is shaped so as to define:
a second circuitry portion, including one or more electronic components, and
an elongate circuitry-connecting portion, which connects the first circuitry portion to the second circuitry portion, and which includes an electrical lead that is integral with the elongate circuitry-connecting portion.

For some applications, the elongate circuitry-connecting portion is oriented circumferentially around a circumferential portion of the frame.

For some applications, the one or more electronic components of the second circuitry portion include an energy storage module.

For some applications, the circuitry portion of the PCB is an end portion of the PCB.

For some applications, the elongate portion of the PCB extends directly from the circuitry portion of the PCB.

For some applications, the elongate portion of the PCB is integral with the circuitry portion the PCB.

For some applications, the electrical lead is fabricated as a track of the elongate portion of the PCB in connection with one or more of the tracks of the PCB are that part of the circuitry.

For some applications:
the elongate portion of the PCB is mechanically coupled to some of the interconnected stent struts of the frame by suturing using sutures, and
the elongate portion of the PCB is shaped so as to define a plurality of protrusions along the elongate portion, which inhibit the sutures from sliding along the elongate portion, such that the sutures fix the elongate portion of the PCB securely to the stent struts.

For some applications, the protrusions protrude laterally from the elongate portion of the PCB in a plane defined by the PCB.

For some applications, an average distance of lateral protrusion of the protrusions beyond non-protruding portions of the elongate portion, in a single direction, equals 20%-100% of widths of the elongate portion of the PCB at respective locations of the protrusions along the elongate portion, the average distance and the widths measured in the plane defined by the PCB.

For some applications, the elongate portion of the PCB is bifurcated, so as to define a main elongate portion and two or more bifurcation elongate portions.

For some applications, the electrical lead is bifurcated, so as to define a main portion and two or more bifurcation portions integral with respective bifurcation elongate portions of the elongate portion of the PCB.

For some applications, the electrical lead is one of a plurality of electrical leads, which are partially integral with the main elongate portion of the elongate portion of the PCB, and partially integral with respective bifurcation elongate portions of the elongate portion of the PCB.

There is additionally provided, in accordance with an application of the present invention, a prosthetic aortic valve, which is configured to be delivered to a native aortic valve of a patient in a constrained delivery configuration, and which includes:
a frame, which defines a central longitudinal axis when the prosthetic aortic valve is in the constrained delivery configuration, and which includes interconnected stent struts arranged so as to define interconnected stent cells;
a plurality of prosthetic leaflets coupled to the frame so as to allow blood flow in a downstream direction and inhibit blood flow in an upstream direction when the prosthetic aortic valve is in an expanded deployment configuration; and an antenna, which is mechanically coupled to the frame downstream of the prosthetic leaflets, and which includes:
  a magnetic core; and
  one or more coils, which are wound about the magnetic core,
wherein, at at least one location along a length of the magnetic core, an outer perimeter of the magnetic core, in a plane perpendicular to the central longitudinal axis of the frame, has:
  (a) a shorter dimension, which is measured along a ray that (i) radiates radially outward from the central longitudinal axis and (ii) intersects a centroid defined by a planar space bound by the outer perimeter, and
  (b) a longer dimension, which is measured perpendicular to the shorter dimension in the plane, and is at least 150% of the shorter dimension.

For some applications, the longer dimension is at least 175% of the shorter dimension.

For some applications, the longer dimension is at least 200% of the shorter dimension.

For some applications, the longer dimension is no more than 400% of the shorter dimension.

For some applications, the longer dimension is no more than 350% of the shorter dimension.

For some applications:
  an external surface of the magnetic core is shaped so as to define an axially-oriented groove,
  at least one of the one or more coils includes a wire, and
  a straight portion of the wire is disposed at least partially within the axially-oriented groove, so as to pass from a first axial end to a second axial end of the at least one of the coils.

For some applications, the prosthetic aortic valve further includes:
  a cathode and an anode, which are mechanically coupled to the frame; and
  circuitry, which is electrically coupled to the cathode, the anode, and the one or more coils.

For some applications, a radially-outward portion of the outer perimeter of the magnetic core, which includes a point on the outer perimeter farthest from the central longitudinal axis, is concavely curved with respect to the central longitudinal axis.

For some applications, the radially-outward portion of the outer perimeter of the magnetic core has a greatest radius of curvature of 1-5 mm.

For some applications, the radially-outward portion of the outer perimeter of the magnetic core has a greatest radius of curvature of 0.3-1.6 times the longer dimension.

For some applications, a radially-inward portion of the outer perimeter, which includes a point on the outer perimeter closest to the central longitudinal axis, is flat.

For some applications, a radially-inward portion of the outer perimeter, which includes one or more points on the outer perimeter closest to the central longitudinal axis, is concavely curved with respect to the central longitudinal axis.

For some applications, the radially-inward portion of the outer perimeter has a greatest radius of curvature that is less than a greatest radius of curvature of the radially-outward portion of the outer perimeter.

For some applications, the curved radially-outward portion of the outer perimeter includes an arcuate portion of a circle.

For some applications, the arcuate portion has a measure of 45-180 degrees.

For some applications, the measure is 60-120 degrees.

For some applications:
  the magnetic core is shaped so as to define a cavity, and
  the prosthetic aortic valve further includes circuitry, which is disposed at least partially within the cavity, and which is electrically coupled to the one or more coils.

For some applications, the circuitry is disposed entirely within the cavity.

For some applications, the magnetic core has an average wall thickness surrounding the cavity of 100-500 microns.

For some applications, the magnetic core has an average wall thickness surrounding the cavity equal to 0.05-0.4 times the shorter dimension.

For some applications, a valve prosthesis system is provided that includes the prosthetic aortic valve and further includes an external unit,
  the one or more coils are one or more prosthetic-valve coils, and
  the external unit is configured to be disposed outside a body of the patient, and includes:
    an energy-transmission coil; and
    external-unit control circuitry, which is configured to drive the energy-transmission coil to wirelessly transfer energy to at least one of the one or more prosthetic-valve coils by inductive coupling.

There is yet additionally provided, in accordance with an application of the present invention, an implantable medical device, which includes:
  an antenna, which includes:
    a magnetic core, which is shaped so as to define a cavity; and
    one or more coils, which are wound about the magnetic core; and
  circuitry, which is disposed at least partially within the cavity, and which is electrically coupled to the one or more coils.

For some applications, the circuitry is disposed entirely within the cavity.

For some applications, the magnetic core has an average wall thickness surrounding the cavity of 100-500 microns.

For some applications, the implantable medical device further includes a cathode and an anode, which are electrically coupled to the circuitry.

For some applications, the implantable medical device includes a prosthetic aortic valve, which is configured to be delivered to a native aortic valve of a patient in a constrained delivery configuration, and which includes:
  a frame, which includes interconnected stent struts arranged so as to define interconnected stent cells; and
  a plurality of prosthetic leaflets coupled to the frame so as to allow blood flow in a downstream direction and inhibit blood flow in an upstream direction when the prosthetic aortic valve is in an expanded deployment configuration,
wherein the antenna is mechanically coupled to the frame.

For some applications, the antenna is mechanically coupled to the frame downstream of the prosthetic leaflets.

For some applications:
  the frame defines a central longitudinal axis when the prosthetic aortic valve is in the constrained delivery configuration, and
  at at least one location along a length of the magnetic core, an outer perimeter of the magnetic core, in a plane perpendicular to the central longitudinal axis of the frame, has:

(a) a shorter dimension, which is measured along a ray that (i) radiates radially outward from the central longitudinal axis and (ii) intersects a centroid defined by a planar space bound by the outer perimeter, and (b) a longer dimension, which is measured perpendicular to the shorter dimension in the plane, and is at least 150% of the shorter dimension.

For some applications, a valve prosthesis system is provided that includes the apparatus and further includes an external unit, the one or more coils are one or more medical-device coils, and the external unit is configured to be disposed outside a body of the patient, and includes:
an energy-transmission coil; and
external-unit control circuitry, which is configured to drive the energy-transmission coil to wirelessly transfer energy to at least one of the one or more medical-device coils by inductive coupling.

There is also provided, in accordance with an application of the present invention, a prosthetic aortic valve, which is configured to be delivered to a native aortic valve of a patient in a constrained delivery configuration, and which includes:

a frame, which defines a central longitudinal axis when the prosthetic aortic valve is in an expanded deployment configuration, and which includes interconnected stent struts arranged so as to define interconnected stent cells;

a plurality of prosthetic leaflets coupled to the frame so as to allow blood flow in a downstream direction and inhibit blood flow in an upstream direction; and an antenna, which is mechanically coupled to the frame downstream of the prosthetic leaflets, and which includes one or more prosthetic-valve coils, first and second downstream peaks respectively defined by circumferentially adjacent first and second downstream-most stent cells of the interconnected stent cells are located at respective first and second peak angular locations about the central longitudinal axis of the frame, and the antenna is mechanically coupled to the frame such that (a) a centroid of the antenna is at an antenna angular location about the central longitudinal axis, the antenna angular location between the first and the second peak angular locations, and (b) a downstream-most point of the antenna is axially disposed between (i) 5 mm downstream of the first and the second downstream peaks and (ii) 5 mm upstream of the first and the second downstream peaks.

For some applications, the antenna is mechanically coupled to the frame such that the downstream-most point of the antenna is axially disposed between (i) 3 mm downstream of the first and the second downstream peaks and (ii) 5 mm upstream of the first and the second downstream peaks.

There is further provided, in accordance with an application of the present invention, a prosthetic aortic valve, which is configured to be delivered to a native aortic valve of a patient in a constrained delivery configuration, and which includes:

a frame, which defines a central longitudinal axis when the prosthetic aortic valve is in an expanded deployment configuration, and which includes:
interconnected stent struts arranged so as to define interconnected stent cells; and one or more delivery-tool-coupling tabs, disposed downstream of the stent cells, and shaped so as to define respective upstream-facing edges;

a plurality of prosthetic leaflets coupled to the frame so as to allow blood flow in a downstream direction and inhibit blood flow in an upstream direction; and an antenna, which is mechanically coupled to the frame downstream of the prosthetic leaflets, and which includes one or more prosthetic-valve coils, wherein first and second downstream peaks respectively defined by circumferentially adjacent first and second downstream-most stent cells of the interconnected stent cells are located at respective first and second peak angular locations about the central longitudinal axis of the frame, and wherein the antenna is mechanically coupled to the frame such that (a) a centroid of the antenna is at an antenna angular location about the central longitudinal axis, the antenna angular location between the first and the second peak angular locations, and (b) a downstream-most point of the antenna is axially disposed between (i) an axial position of the upstream-facing edges of the delivery-tool-coupling tabs and (ii) 5 mm upstream of the first and the second downstream peaks.

For some applications, a valve prosthesis system is provided that includes the prosthetic aortic valve and further includes a delivery system, which includes a delivery shaft that is removably couplable to the one or more delivery-tool-coupling tabs.

For some applications, the antenna includes a magnetic core around which are wound the one or more prosthetic-valve coils.

For some applications:
the first and the second downstream-most stent cells are joined at a cell junction,
the first downstream-most stent cell includes a right downstream strut of the interconnected stent struts, the right downstream strut extending between the cell junction and a first downstream peak defined by the first downstream-most stent cell,
the second downstream-most stent cell includes a left downstream strut of the interconnected stent struts, the left downstream strut extending between the cell junction and a second downstream peak defined by the second downstream-most stent cell,
a flexible sheet is mechanically coupled to the right and the left downstream struts, and
the antenna is mechanically coupled to the frame at least in part by being mechanically coupled to the flexible sheet between the right and the left downstream struts.

For some applications, the first and the second downstream-most stent cells are joined at a cell junction, and the antenna is mechanically coupled to the frame at least in part by being mechanically coupled to the cell junction.

For some applications, an upstream-most point of the antenna coincides with, or is no more than a distance upstream of, the cell junction, the distance equal to 30% of a length of the antenna, the distance and the length measured parallel to the central longitudinal axis of the frame.

For some applications:
the first and the second peak angular locations are angularly offset by a peak-to-peak angular offset,
the first peak angular location and the antenna angular location are angularly offset by a peak-to-antenna angular offset, and
the peak-to-antenna angular offset equals 25%-75% of the peak-to-peak angular offset.

For some applications, the downstream-most point of the antenna is axially disposed between 5 mm downstream of the first and the second downstream peaks and 5 mm upstream of the first and the second downstream peaks.

For some applications:
the circumferentially adjacent first and second downstream-most stent cells are joined at a cell junction,
a peak height equals a distance between a downstream-most point of the first downstream peak and the cell junction, measured parallel to the central longitudinal axis of the frame, and
a length of the antenna equals 30%-150% of the peak height, the length and the peak height measured parallel to the central longitudinal axis of the frame.

For some applications:
the first and the second peak angular locations are angularly offset by a peak-to-peak angular offset, and
a width of the antenna, measured in a peak-to-peak direction, equals 10%-60% of the peak-to-peak angular offset.

For some applications, the prosthetic aortic valve further includes:
a cathode and an anode, which are mechanically coupled to the frame; and
circuitry, which is electrically coupled to the cathode, the anode, and the one or more prosthetic-valve coils.

For some applications, a valve prosthesis system is provided that includes the prosthetic aortic valve and further includes an external unit, the external unit is configured to be disposed outside a body of the patient, and includes:
an energy-transmission coil; and
external-unit control circuitry, which is configured to drive the energy-transmission coil to wirelessly transfer energy to at least one of the one or more prosthetic-valve coils by inductive coupling.

There is still further provided, in accordance with an application of the present invention, a prosthetic aortic valve, which is configured to be delivered to a native aortic valve of a patient in a constrained delivery configuration, and which includes:
a frame, which defines a central longitudinal axis when the prosthetic aortic valve is in an expanded deployment configuration, and which includes interconnected stent struts arranged so as to define interconnected stent cells;
a plurality of prosthetic leaflets coupled to the frame so as to allow blood flow in a downstream direction and inhibit blood flow in an upstream direction;
an antenna, which is mechanically coupled to the frame downstream of the prosthetic leaflets, and which includes one or more prosthetic-valve coils; and
a flexible sheet,
wherein circumferentially adjacent first and second downstream-most stent cells of the interconnected stent cells are joined at a cell junction,
wherein the first downstream-most stent cell includes a right downstream strut of the interconnected stent struts, the right downstream strut extending between the cell junction and a first downstream peak defined by the first downstream-most stent cell,
wherein the second downstream-most stent cell includes a left downstream strut of the interconnected stent struts, the left downstream strut extending between the cell junction and a second downstream peak defined by the second downstream-most stent cell,
wherein the flexible sheet is mechanically coupled to the right and the left downstream struts, and
wherein the antenna is mechanically coupled to the frame at least in part by being mechanically coupled to the flexible sheet between the right and the left downstream struts.

For some applications, the antenna is mechanically coupled to the frame at least in part by being mechanically coupled to the cell junction.

For some applications, the antenna is mechanically coupled to the flexible sheet by stitching.

For some applications, the flexible sheet is mechanically coupled to the right and the left downstream struts by stitching.

For some applications, the antenna includes a magnetic core around which are wound the one or more coils.

There is additionally provided, in accordance with an application of the present invention, a prosthetic aortic valve system including a prosthetic aortic valve, which is configured to be delivered to a native aortic valve of a heart of a patient in a constrained delivery configuration, and which includes:
a frame;
a plurality of prosthetic leaflets coupled to the frame so as to allow blood flow in a downstream direction and inhibit blood flow in an upstream direction when the prosthetic aortic valve is in an expanded deployment configuration;
electrodes, which include one or more cathodes and one or more anodes, which are mechanically coupled to the frame; and
circuitry, which is electrically coupled to the electrodes, and which is configured to apply pacing to the heart using a subset of the electrodes that includes fewer than all of the electrodes, at least one of the one or more cathodes, and at least one of the one or more anodes.

For some applications, the prosthetic aortic valve system is configured to select the subset of the electrodes by separately activating different combinations of the electrodes at different times, and selecting the subset of the electrodes that provides most effective pacing.

For some applications, the prosthetic aortic valve is configured to sense an ECG of the heart, and the prosthetic aortic valve system is configured to select the subset of the electrodes based on the ECG sensed when separately activating the different combinations of the electrodes at the different times.

For some applications, the prosthetic aortic valve system is configured to select the subset of the electrodes by separately activating different combinations of the electrodes before the circuitry applies each pulse of the pacing.

For some applications, the circuitry of the prosthetic aortic valve is configured to select the subset of the electrodes.

For some applications, the circuitry is prosthetic-aortic-valve circuitry, and the prosthetic aortic valve system includes an external control unit, which includes external circuitry that is configured to select the subset of the electrodes.

There is yet additionally provided, in accordance with an application of the present invention, a valve prosthesis system for use with a guidewire, the valve prosthesis system including:
(i) a prosthetic aortic valve, which is configured to be delivered to a native aortic valve of a patient in a constrained delivery configuration using the guidewire, and which includes:

(a) a frame;
(b) a plurality of prosthetic leaflets coupled to the frame;
(c) a cathode and an anode, which are mechanically coupled to the frame; and
(d) an antenna, which includes one or more prosthetic-valve coils, and which is in electrical communication with the cathode and the anode; and (ii) an external unit, which is configured to be disposed outside a body of the patient, and which includes:
(a) a housing, which is shaped so as to define a guidewire-receiving channel;
(b) a rapid-pacing user control;
(c) an energy-transmission coil; and
(d) external-unit control circuitry, which is configured to:
drive the energy-transmission coil to wirelessly transfer energy to at least one of the one or more prosthetic-valve coils by inductive coupling, and
only upon activation of the rapid-pacing user control and when the guidewire is disposed within the guidewire-receiving channel of the housing, drive the prosthetic aortic valve to apply rapid pacing using the cathode and the anode.

There is also provided, in accordance with an application of the present invention, apparatus including an implantable medical device, which includes:
an antenna, which includes:
an elongate core; and
first, second, and third coils, wound around the elongate core such that:
the first coil encircles a first-coil longitudinal axis that coincides with a central longitudinal axis of the elongate core,
the second coil encircles a second-coil longitudinal axis that is perpendicular to the first-coil longitudinal axis, and
the third coil encircles a third-coil longitudinal axis that is perpendicular to the first-coil longitudinal axis and to the second-coil longitudinal axis,
wherein the second and the third coils cross each other at both longitudinal ends of the elongate core,
wherein the second coil has two longer sides and two shorter sides, and
wherein the two longer sides are parallel to the central longitudinal axis of the elongate core, or define an angle of less than 10 degrees with respect to the central longitudinal axis of the elongate core.

For some applications:
the third coil has two longer sides and two shorter sides, and
the two longer sides of the third coil are parallel to the central longitudinal axis of the elongate core, or define an angle of less than 10 degrees with respect to the central longitudinal axis of the elongate core.

For some applications, the two longer sides cross the first coil at a plurality of first locations, and define angles of 75-90 degrees with the first coil at each of the plurality of first locations.

For some applications:
the third coil has two longer sides and two shorter sides, and
the two longer sides of the third coil cross the first coil at a plurality of second locations, and define angles of 75-90 degrees with the first coil at each of the plurality of second locations.

For some applications:
an external surface of the elongate core is shaped so as to define an axially-oriented groove,
the first coil includes a wire, and
a straight portion of the wire is disposed at least partially within the axially-oriented groove, so as to pass from a first axial end to a second axial end of the first coil.

The present invention will be more fully understood from the following detailed description of embodiments thereof, taken together with the drawings, in which:

BRIEF DESCRIPTION OF THE DRAWINGS

FIGS. 3A-C are schematic illustrations of a printed circuit board (PCB), an electrical lead, and electrodes, in accordance with an application of the present invention;

FIG. 3D is a schematic illustration of a portion of the prosthetic aortic valve of FIGS. 1A-B and the PCB of FIGS. 3A-C coupled to stent struts of the prosthetic aortic valve, in accordance with an application of the present invention;

FIG. 3H is a schematic illustration of yet another configuration of a frame of the prosthetic aortic valve of FIGS. 1A-B and the PCB of FIGS. 3A-C coupled to the frame, in accordance with an application of the present invention;

DETAILED DESCRIPTION OF APPLICATIONS

Figure 1:
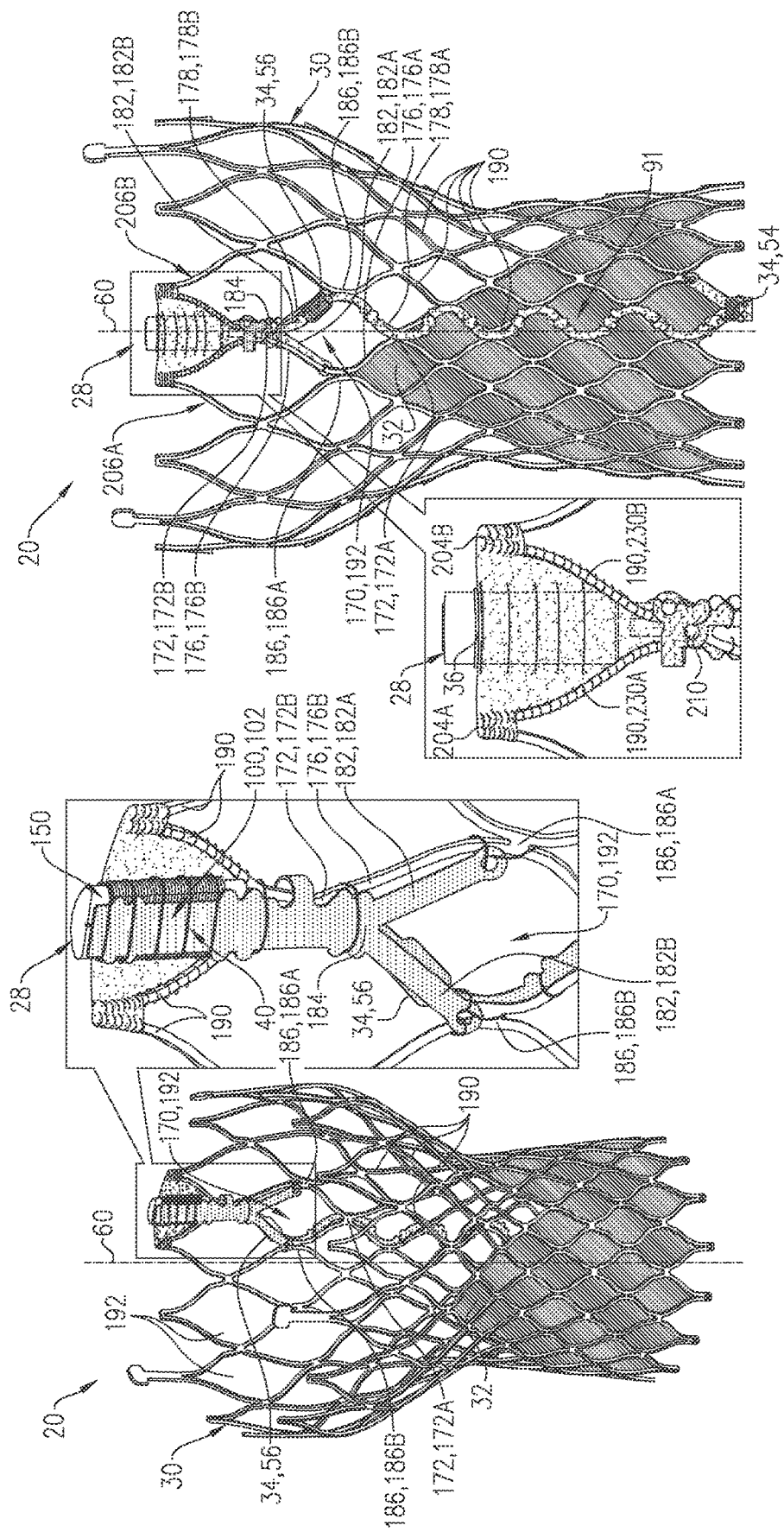
FIGS. 1A and 1B are schematic illustrations a prosthetic aortic valve, in accordance with an application of the present invention.

Reference is made to FIGS. 1A and 1B, which are schematic illustrations of a prosthetic aortic valve 20, in accordance with an application of the present invention. For clarity of illustration, only the closer half of prosthetic aortic valve 20 is shown in FIG. 1B.

Figure 2:
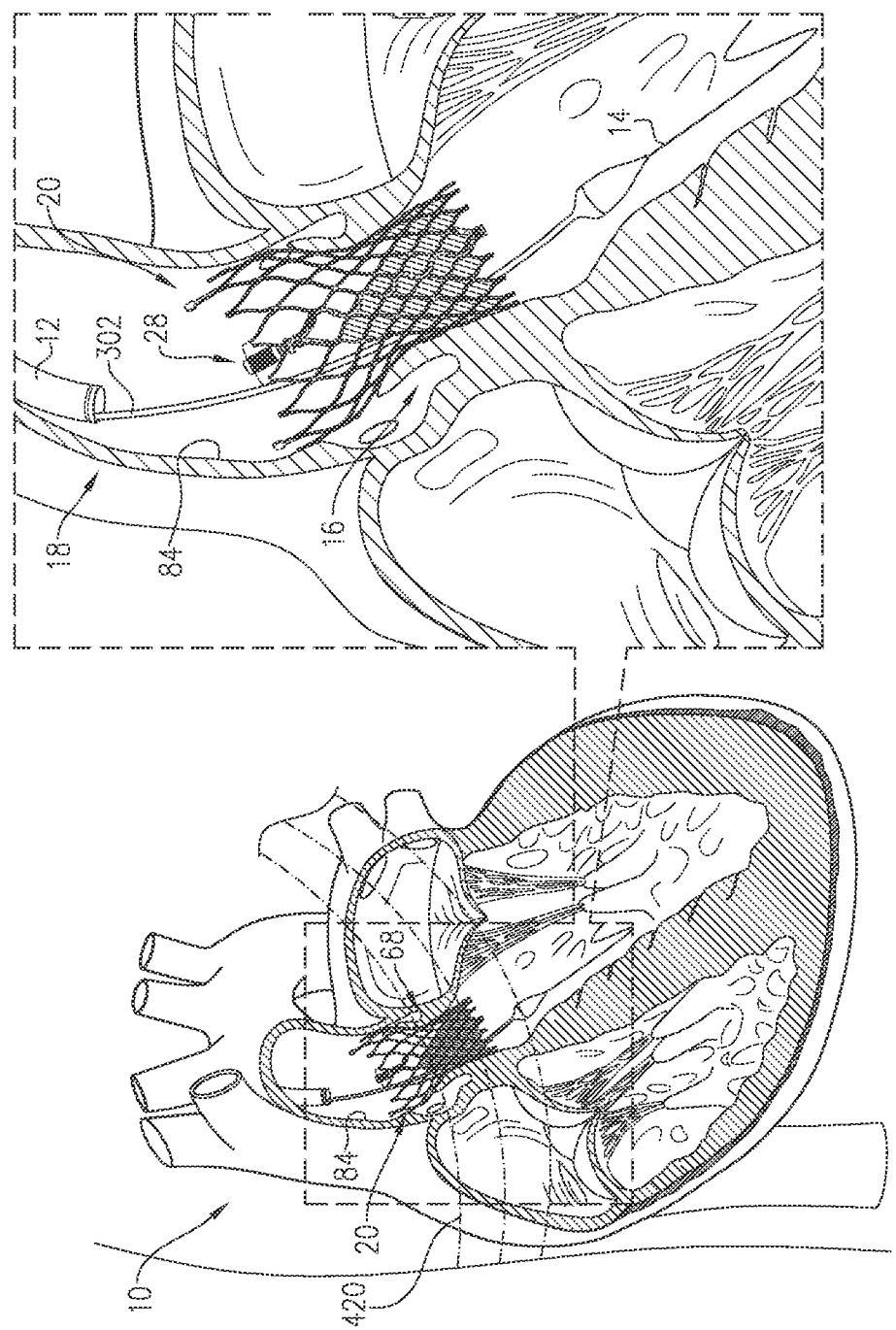
FIG. 2 is a schematic illustration of a valve prosthesis system and the prosthetic aortic valve of FIGS. 1A-B implanted in a body of a patient, in accordance with an application of the present invention.

Reference is also made to FIG. 2, which is a schematic illustration of a valve prosthesis system 10 and prosthetic aortic valve 20 implanted in a body of a patient, in accordance with an application of the present invention. Valve prosthesis system 10 further comprises a delivery system 18, which typically comprises a delivery sheath 12 and is used with a guidewire 14. Prosthetic aortic valve 20 is typically configured to be delivered to a native aortic valve 16 of the patient in a constrained delivery configuration within delivery sheath 12. Typically, prosthetic aortic valve 20 is deployed using imaging, such as fluoroscopy, and is rotated if necessary during the deployment such that a cathode 54 is disposed against tissue of the annulus that is near the bundle of His.

Prosthetic aortic valve 20 is shown in FIGS. 1A-B and FIG. 2 in an expanded configuration. Frame 30 defines a central longitudinal axis 60 when prosthetic aortic valve 20 is in this expanded deployment configuration.

Prosthetic aortic valve 20 comprises:
a frame 30;
a plurality of prosthetic leaflets 32 coupled to frame 30 so as to allow blood flow in a downstream direction and inhibit blood flow in an upstream direction when prosthetic aortic valve 20 is in the expanded deployment configuration, such as shown in FIGS. 1A-B and 2;
an antenna 28, which is mechanically coupled to frame 30, and which comprises one or more prosthetic-valve coils 36;
one or more electrodes 34, such as cathode 54 and an anode 56, coupled to frame 30; and
optionally, circuitry 40, which is electrically coupled to cathode 54, anode 56, and the one or more prosthetic-valve coils 36.

Typically, circuitry 40 is configured to apply pacing to the heart using the one or more electrodes 34. For example, the pacing may be applied temporarily for up to several weeks after implantation of prosthetic aortic valve 20 (e.g., up to one month after implantation), typically using an external control unit to continuously provide power, such as external control unit 400, described hereinbelow with reference to FIG. 10. Alternatively, for some applications, the pacing is applied longer-term, in which case prosthetic aortic valve 20 may further comprise an energy storage module, e.g., comprising a battery, which may be periodically charged using the external control unit, which may obviate the need for the patient to constantly wear an external energy transmitter. For example, the pacing may comprise ongoing sensing of a native electrical signal of the heart and deliverance of electrical stimulus in cases in which the native signal is unsatisfactory for timely ventricular contraction ("VVI pacing"). Further alternatively or additionally, for some applications, circuitry 40 is configured to apply rapid pacing during an invasive structural heart procedure, such as an implantation procedure, such as a TAVR-in-TAVR procedure in which the first TAVR comprises prosthetic aortic valve 20.

For some applications, prosthetic aortic valve 20 is configured to sense an electrocardiography (ECG) of the patient's heart. Circuitry 40 may be configured to sense the ECG, or separate circuitry may be provided for sensing the ECG. The ECG sensing may be performed using all or a subset of electrodes 34 and/or one or more separate electrodes may be provided for performing the ECG sensing.

Frame 30 typically comprises a stent or other structure, which is typically self-expanding, and may be formed by laser cutting or etching a metal alloy tube comprising, for example, stainless steel or a shape memory material such as Nitinol. For some applications, frame 30 comprises interconnected stent struts 190 arranged so as to define interconnected stent cells 192. Optionally, interconnected stent cells 192 are generally diamond-shaped, such as shown in the drawings.

Typically, adjoining pairs of prosthetic leaflets 32 are attached to one another at their lateral ends to form commissures, with free edges of the prosthetic leaflets forming coaptation edges that meet one another. Prosthetic leaflets 32 typically comprise a sheet of animal pericardial tissue, such as porcine pericardial tissue, or synthetic or polymeric material. Optionally, prosthetic aortic valve 20 further comprises a skirt.

For some applications, cathode 54 has a thickness of at least 10 microns, no more than 200 microns, and/or between 10 and 200 microns, e.g., about 50 microns, and/or a surface area of at least 0.5 mm$^2$, e.g., at least 1 mm$^2$; no more than 20 mm$^2$; and/or 0.5-20 mm$^2$, such as 1-20 mm$^2$, in order to provide adequate stimulation. For some applications, cathode 54 is coated with titanium nitride (TiN).

Typically, antenna 28 is mechanically coupled to frame 30 downstream of prosthetic leaflets 32.

Reference is made to FIGS. 1A-B. For some applications:
circumferentially adjacent first and second downstream-most stent cells 206A and 206B of interconnected stent cells 192 are joined at a cell junction 210 (labeled in FIG. 1B and better seen in FIG. 9, described hereinbelow),
first downstream-most stent cell 206A comprises a right downstream strut 230A of interconnected stent struts 190, right downstream strut 230A extending between cell junction 210 and a first downstream peak 204A defined by first downstream-most stent cell 206A, and
second downstream-most stent cell 206B comprises a left downstream strut 230B of interconnected stent struts 190, left downstream strut 230B extending between cell junction 210 and a second downstream peak 204B defined by second downstream-most stent cell 206B.

For some applications, prosthetic aortic valve 20 further comprises a flexible sheet 62, which is mechanically coupled to right and left downstream struts 230A and 230B. Optionally, flexible sheet 62 is mechanically coupled to right and left downstream struts 230A and 230B by stitching, such as shown; alternatively or additionally, flexible sheet 62 is mechanically coupled to right and left downstream struts 230A and 230B using alternative coupling techniques that are known in the art.

Flexible sheet 62 may comprise, for example, a polymer (e.g., polyethylene terephthalate (PET) or expanded Polytetrafluoroethylene (ePTFE)) or biological tissue, e.g., a pericardium sheet. Optionally, the material of flexible sheet 62 is woven. Optionally, the material of flexible sheet 62 comprises cloth. Flexible sheet 62 is collapsible with prosthetic aortic valve 20 when loaded into delivery sheath 12.

Antenna 28 is mechanically coupled to frame 30 at least in part by being mechanically coupled to flexible sheet 62 between right and left downstream struts 230A and 230B. Optionally, antenna 28 is mechanically coupled to flexible sheet 62 by stitching, such as shown; alternatively or additionally, antenna 28 is mechanically coupled to flexible sheet 62 using alternative coupling techniques that are known in the art. (Because flexible sheet 62 and antenna 28 are shown from outside prosthetic aortic valve 20 in FIG. 1B, flexible sheet 62 partially obscures the view of antenna 28.)

Optionally, antenna 28 is mechanically coupled to frame 30 at least in part by being mechanically coupled to cell junction 210.

For some applications, flexible sheet 62 has an area of 25-100 mm^2.

For some applications, flexible sheet 62 is coupled only to one or more interconnected stent struts 190 of each of first and second downstream-most stent cells 206A and 206B, and not to any interconnected stent struts 190 of other stent cells of frame 30.

For some applications, flexible sheet 62 has three sides.

Typically, flexible sheet 62 is separate and distinct from material of prosthetic leaflets 32.

Figures 3C, 3D:
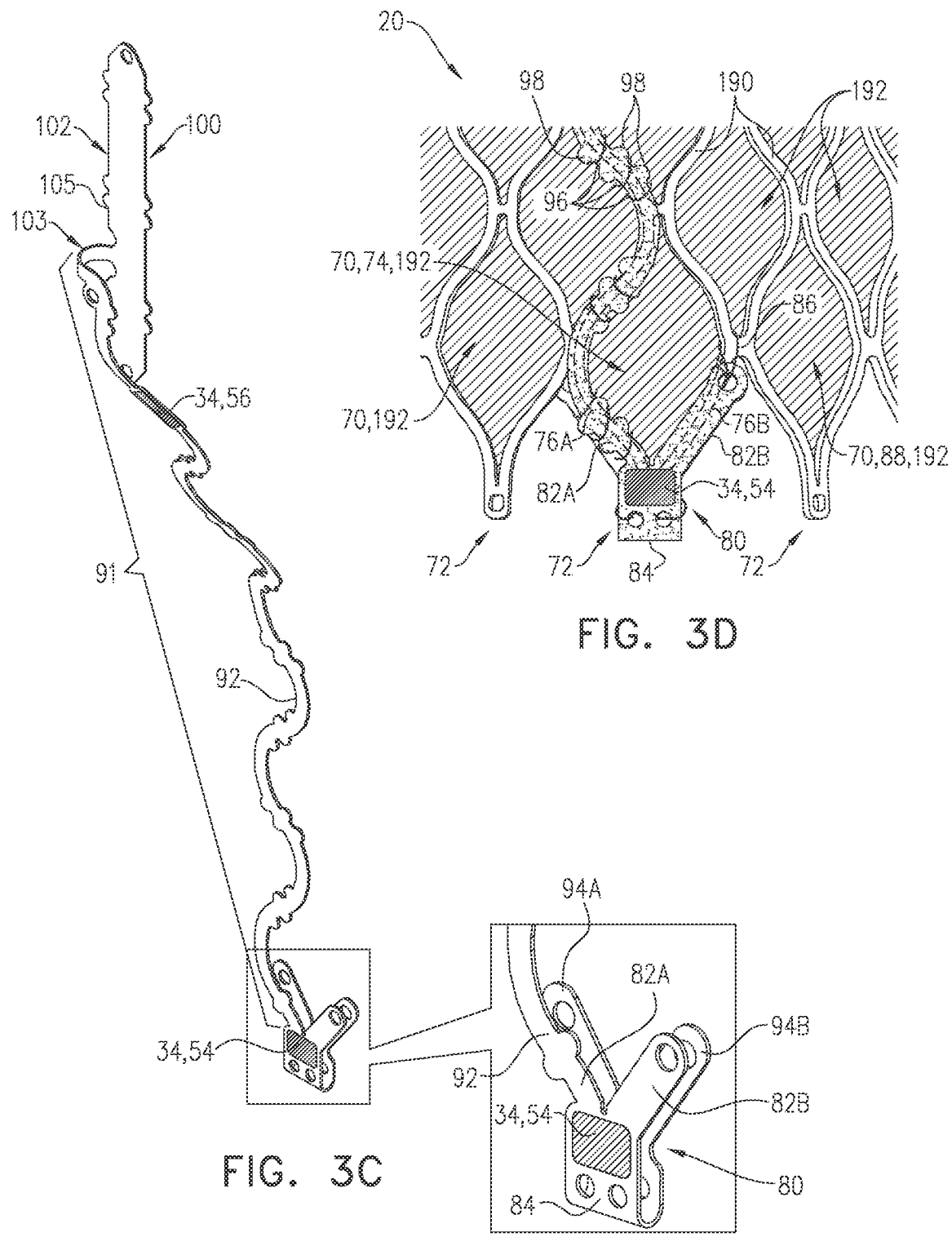

Reference is now made to FIGS. 3A-C, which are schematic illustrations of a printed circuit board (PCB) 92, an electrical lead 90, and electrodes 34, in accordance with an application of the present invention. PCB 92 typically comprises a polymer, such as polyimide, as is known the PCB art. PCB 92 is typically flexible.

Reference is also made to FIG. 3D, which is a schematic illustration of a portion of prosthetic aortic valve 20 and PCB 92 coupled to stent struts 190, in accordance with an application of the present invention.

Figure 3E:
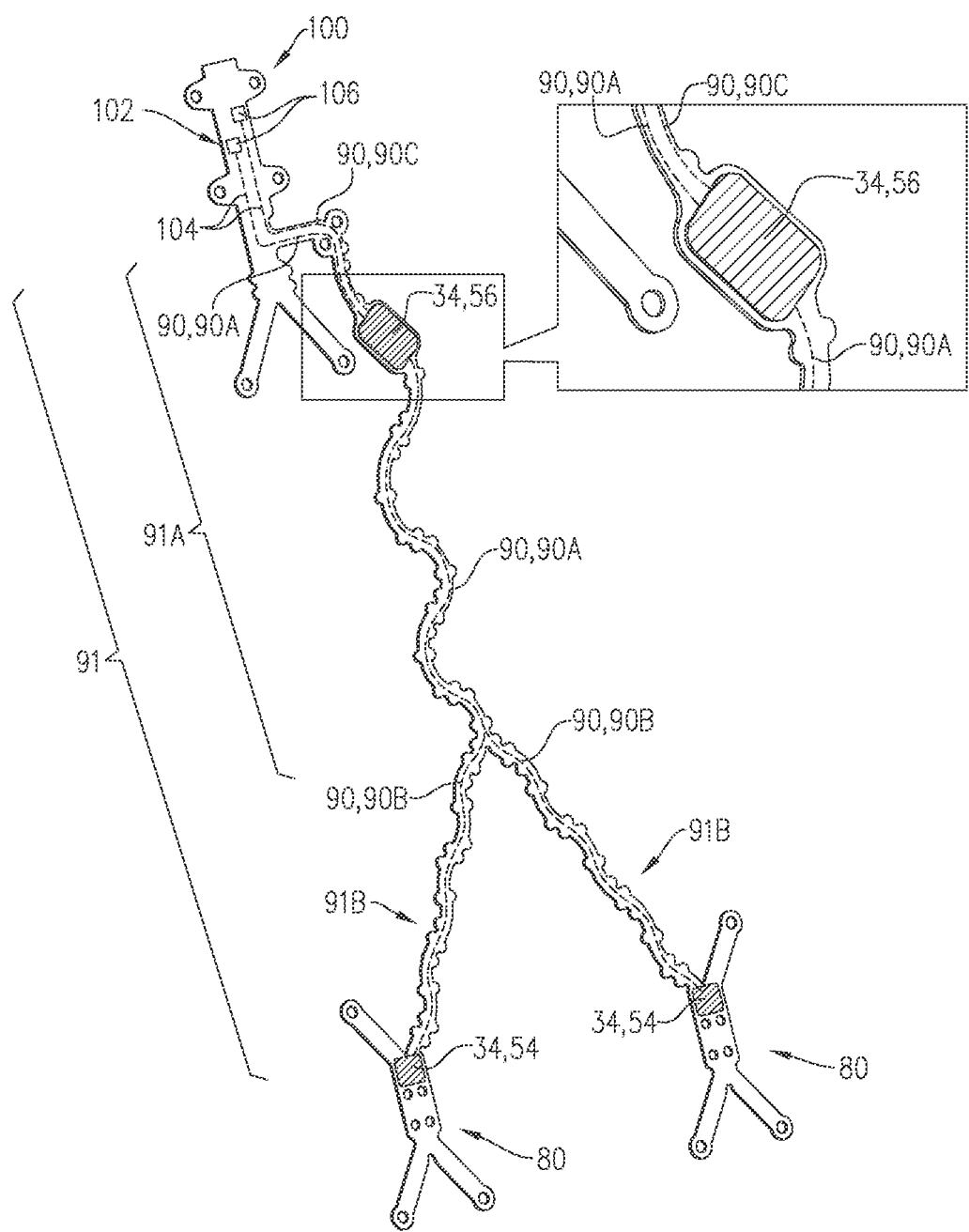
FIGS. 3E and 3F are schematic illustrations additional configurations of the PCB of FIGS. 3A-C, in accordance with respective applications of the present invention.
Figure 3F:
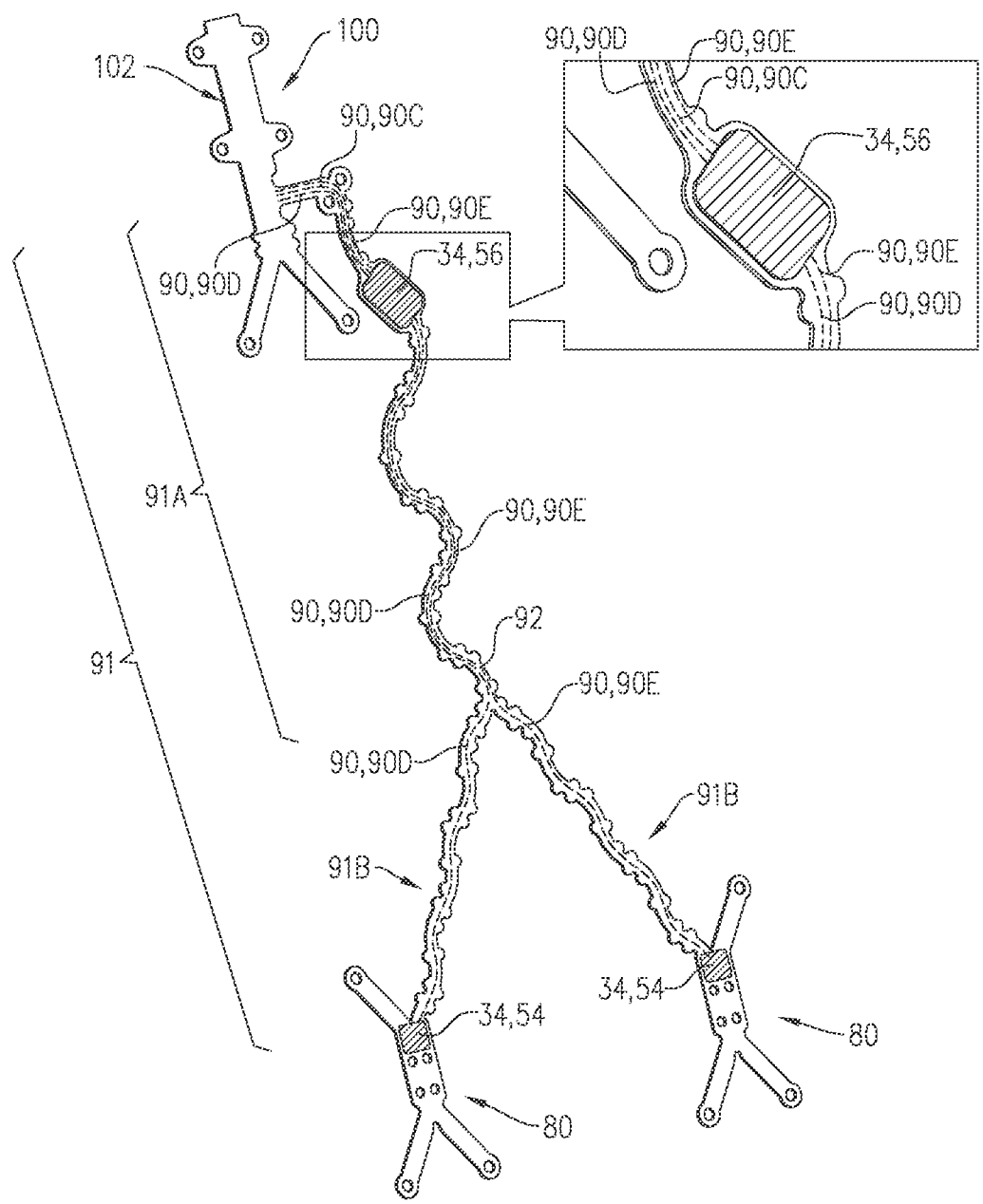

Reference is further made to FIGS. 3E and 3F, which are schematic illustrations additional configurations of PCB 92, in accordance with respective applications of the present invention.

Figure 3G:
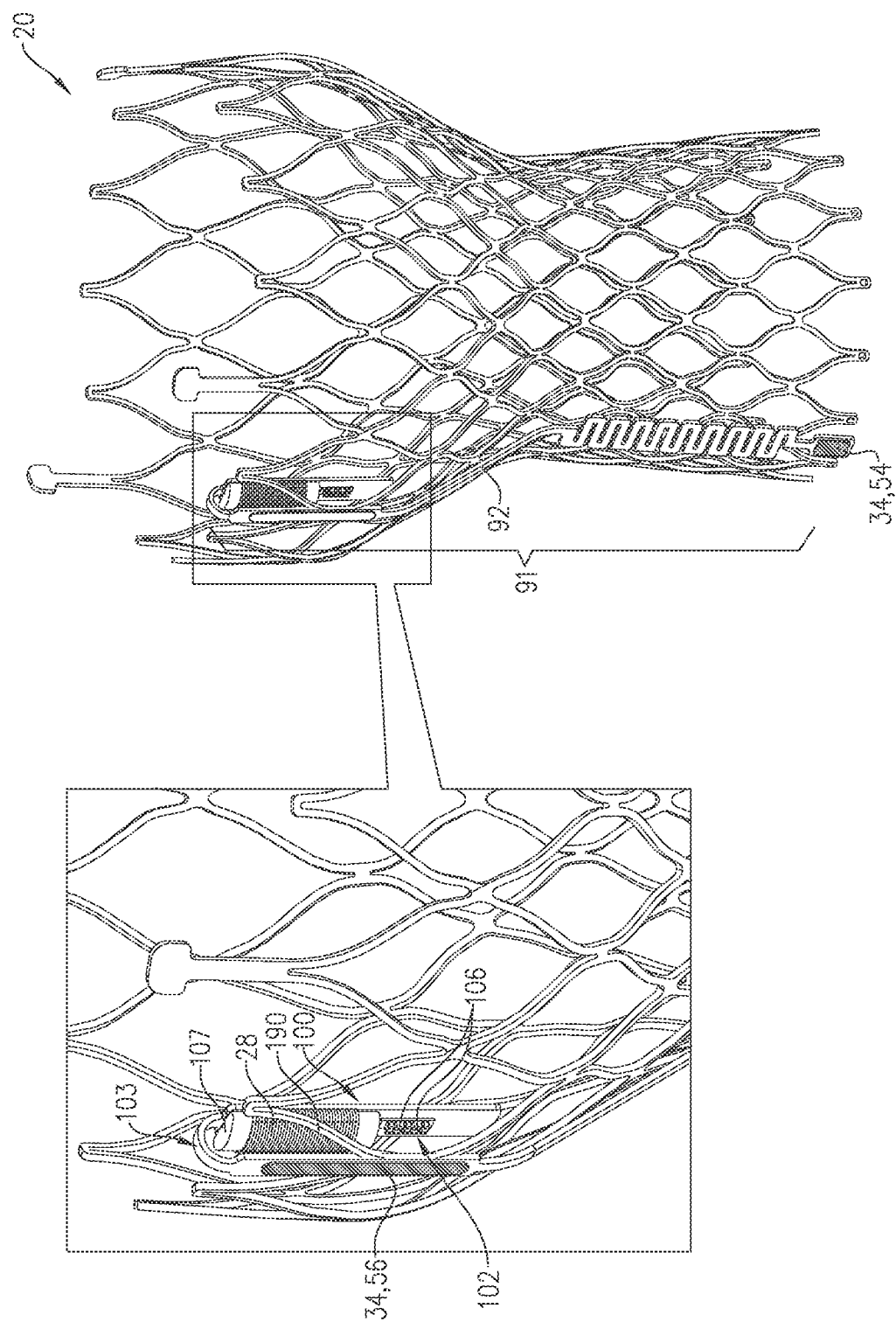
FIG. 3G is a schematic illustration of another configuration of the PCB of FIGS. 3A-C, in accordance with an application of the present invention.

Reference is still further made to FIG. 3G, which is a schematic illustration of another configuration of PCB 92, in accordance with an application of the present invention.

Reference is additionally made to FIG. 3H, which is a schematic illustration of frame 30 of prosthetic aortic valve 20 and yet another configuration of PCB 92 coupled to frame 30, in accordance with an application of the present invention.

FIGS. 3A-C, 3E-F, and 3H show elements of prosthetic aortic valve 20 prior to assembly of prosthetic aortic valve 20, and FIGS. 3D and 3G show these elements after assembly of prosthetic aortic valve 20.

In some of the configurations shown in FIGS. 3A-F and 3H, upstream ones 70 of interconnected stent cells 192 are located in an upstream half of frame 30 and define respective upstream peaks 72. At least one electrode 34, such as a cathode 54, is disposed at or near (e.g., within 8 mm of) an upstream peak 72 of one 74 of the upstream stent cells 70. First and second upstream stent struts 76A and 76B of the one 74 of upstream stent cells 70 are joined at the upstream peak 72 (the upstream peak 72 is obscured in FIG. 3D, but can be seen in the adjacent stent cells). Optionally, such as shown, the upstream ones 70 of stent cells 192 are upstream-most ones of stent cells 192, and the one 74 of upstream stent cells 70 is one 74 of upstream-most stent cells 192. Alternatively, the upstream ones 70 of stent cells 192 are not upstream-most ones of stent cells 192, and the one 74 of upstream stent cells 70 is not one 74 of upstream-most stent cells 192 (configuration not shown).

In some of the configurations shown in FIGS. 3A-F and 3H, prosthetic aortic valve 20 further comprises coupling material 80, which is shaped so as to define:

- a first strip 82A that is mechanically coupled to first upstream stent strut 76A,
- a second strip 82B that is mechanically coupled to second upstream stent strut 76B, and
- a junction 84, which couples together first and second strips 82A and 82B, such that first and second strips 82A and 82B together couple electrode 34, such as a cathode 54, to frame 30 at or near (e.g., within 8 mm of) upstream peak 72. Using first and second strips 82A and 82B in this arrangement to couple electrode 34 to frame 30 typically helps stabilize electrode 34 with respect to frame 30, both during expansion of frame 30 from its compressed elongated state, and during many cardiac cycles after implantation of frame 30.

Optionally, first and second strips 82A and 82B are integrally joined at junction 84, e.g., integrally formed from a single piece of material (such as shown); alternatively, first and second strips 82A and 82B comprise discrete pieces of material coupled together at junction 84 (configuration not shown). First strip 82A may be mechanically coupled to either surface of first upstream stent strut 76A, and second strip 82B may be mechanically coupled to either surface of second upstream stent strut 76B.

For some applications, first and second strips 82A and 82B are mechanically coupled to first and second upstream stent struts 76A and 76B, respectively, by stitching, such as shown (to this end, first and second strips 82A and 82B may comprise stitching holes, as shown).

For some applications, junction 84 of coupling material 80 is mechanically coupled to frame 30 at or near (e.g., within 5 mm of) upstream peak 72.

For some applications:

- first strip 82A has length equal to at least 50% of a length of first upstream stent strut 76A; for example, the length of first strip 82A may be greater than the length of first upstream stent strut 76A, such as at least 120% of the length of first upstream stent strut 76A (which may aid with mechanically coupling first strip 82A to first upstream stent strut 76A), and/or
- second strip 82B has length equal to at least 50% of a length of second upstream stent strut 76B, such as least 75%, e.g., 100% of the length of second upstream stent strut 76B, and/or no more than 100% of the length of second upstream stent strut 76B.

For some applications, the one 74 of upstream stent cells 70 is a first one 74 of upstream stent cells 70, and the first one 74 of upstream stent cells 70 is joined at a cell junction 86 (node) to a circumferentially-adjacent second one 88 of upstream stent cells 70. Second strip 82B is mechanically coupled to cell junction 86, such as by stitching, such as shown (to this end, second strip 82B may comprise a stitching hole, as shown).

For some applications, prosthetic aortic valve 20 further comprises electrical lead 90 (shown schematically in the enlargement in FIG. 3A), which is electrically coupled to electrode 34 (and typically circuitry 40, if provided). First strip 82A is mechanically coupled to at least a portion of electrical lead 90.

For some of these applications, first strip 82A comprises electrical insulation, and first strip 82A electrically insulates the at least a portion of electrical lead 90 (such that first strip 82A and electrical lead 90 together provide an electrode lead). For some of these applications, first strip 82A comprises an elongate portion 91 of PCB 92 with which electrical lead 90 is integral (e.g., encased within PCB 92, such as by lamination, or disposed on an external surface of PCB 92 and coated with an electrically insulating coating). Typically, electrical lead 90 comprises a track (also known as a conductive trace) of PCB 92. In this configuration, PCB 92 typically also defines second strip 82B and junction 84 of coupling material 80. Although elongate portion 91 of PCB 92 is shown as oriented in a generally upstream-downstream orientation, elongate portion 91 of PCB 92 may also be at least partially oriented in a circumferential orientation around a portion of frame 30, such as shown in FIG. 3H, in which PCB 92 is shaped so as to define a generally upstream-downstream oriented elongate portion labeled 91, as well as a circumferentially-oriented elongate portion oriented circumferentially around a circumferential portion of frame 30 (horizontal in the figure).

Alternatively, first strip 82A is non-electrically-insulating, in which case electrical lead 90 may be electrically insulated by separate electrical insulation.

For some applications, first and second strips 82A and 82B are outer first and second strips 82A and 82B, which are mechanically coupled to radially outer (with respect to central longitudinal axis 60 of frame 30) sides of first and second upstream stent struts 76A and 76B, respectively. Coupling material 80 is shaped so as to further define:
   an inner first strip 94A that is mechanically coupled to a radially inner side of first upstream stent strut 76A, and
   an inner second strip 94B that is mechanically coupled to a radially inner side of second upstream stent strut 76B.

Junction 84 of coupling material 80 couples together outer first strip 82A, outer second strip 82B, inner first strip 94A, and inner second strip 94B. Outer first strip 82A, outer second strip 82B, inner first strip 94A, and inner second strip 94B together couple electrode 34 to frame 30 at or near upstream peak 72.

For some of these applications, junction 84 of coupling material 80 is folded over upstream peak 72, such as shown, such as shown in FIGS. 3C-D. Optionally, the folded junction 84 is mechanically coupled to frame 30 at or near upstream peak 72, such as by stitching, such as shown (to this end, junction 84 may comprise stitching holes 95, as shown). Prior to being folded over during assembly of prosthetic aortic valve 20, junction 84 may generally have an X-shape, such as shown in FIGS. 3A-B. A fold line 93 is schematically labeled in the enlargement of FIG. 3A.

Reference is still made to FIGS. 3A-D, and is again made to FIGS. 1A-B. For some applications, electrical lead 90, which electrically couples one or more electrodes 34 to circuitry 40, is integral with elongate portion 91 of PCB 92 (electrical lead 90 is shown schematically in the enlargement of FIG. 3A). As shown in FIGS. 1A-B and 3D, elongate portion 91 of PCB 92 is mechanically coupled to some of interconnected stent struts 190 of frame 30, such as by suturing using sutures 96. Elongate portion 91 of PCB 92 thus serves both to provide electrical insulation to electrical lead 90 and to facilitate coupling of electrical lead 90 to stent struts 190. This encasing of electrical lead 90 in elongate portion 91 of PCB 92 may be implemented either in combination with the techniques for mechanically coupling junction 84 to frame 30 at or near upstream peak 72 described above with reference to FIGS. 3A-D, or independently of these techniques.

For some applications, elongate portion 91 of PCB 92 has an undulating shape that generally runs along interconnected stent struts 190, such as shown in FIGS. 1A-B, 3D.

As mentioned above, electrical lead 90 is coupled to electrode 34. For some applications, electrical lead 90 is coupled to cathode 54, while for other applications, electrical lead 90 is coupled to anode 56. Optionally, more than one electrical lead 90 is integral with elongate portion 91 of PCB 92, in which case a first one of electrical leads 90 may be coupled to cathode 54 and a second one of electrical leads 90 may be coupled to anode 56.

Optionally, a plurality of electrical leads 90 are integral with a corresponding plurality of elongate portions of PCB 92, such as described hereinbelow with reference to FIGS. 3E and 3F.

Optionally, one or more electrodes 34, e.g., one or more cathodes 54 and/or one or more anodes 56, are formed integrally with PCB 92.

Typically, both stent struts 190 and elongate portion 91 of PCB 92 are rectangular in cross section taken perpendicular to respective longitudinal axes of the stent struts and the elongate portion. Typically, electrical lead 90 is also rectangular in cross section, or trapezoidal in cross section. These rectangular cross sections enable flush coupling and/or good crimping of elongate portion 91 to stent struts 190.

For some applications:
   stent struts 190 have a thickness of at least 150 microns, such as at least 300 microns; no more than 500 microns; and/or 150-500 microns, such as 300-500 microns,
   stent struts 190 have a width of 200-700 microns,
   a ratio of the width to the thickness of stent struts 190 is 0.5-2,
   electrical lead 90 has a thickness of 5-80 microns, e.g., 50 microns,
   electrical lead 90 has a width of 50-300 microns,
   a ratio of the width to the thickness of electrical lead 90 is 5-50,
   elongate portion 91 of PCB 92 has a thickness of at least 50 microns, no more than 150 microns, and/or 50-150 microns, and/or
   elongate portion 91 of PCB 92 has a width of 300-1500 microns, and/or
   a ratio of the width to the thickness of elongate portion 91 of PCB 92 is 3-20.

Alternatively or additionally, for some applications:
   a ratio of a thickness of stent struts 190 to a thickness of electrical lead 90 is at least 5, no more than 15, and/or 5-15, and/or
   a ratio of a thickness of stent struts 190 to a thickness of elongate portion 91 of PCB 92 is at least 2, no more than 5, and/or 2-5.

Elongate portion 91A and/or bifurcation elongate portions 91B of PCB 92, described hereinbelow with reference to FIGS. 3E and/or 3F, may also have the dimensions provided immediately above for elongate portion 91 of PCB 92. Similarly, main portion 90A of electrical lead 90, bifurcation portions 90B of electrical lead 90, electrical lead 90C, electrical lead 90D, and/or electrical lead 90E, described hereinbelow with reference to FIGS. 3E and/or 3F, may also have the dimensions provided immediately above for electrical lead 90.

For some applications, as shown highly schematically in FIG. 3E, circuitry 40 comprises (a) a circuitry portion 100 of PCB 92, such as an end portion 102 of PCB 92, (b) tracks 104 (also known as conductive traces) of PCB 92, (c) conductive pads of PCB 92, and (d) electronic components 106 coupled to PCB 92. Elongate portion 91 extends directly from circuitry portion 100 (e.g., end portion 102), and is typically integral with circuitry portion 100 (e.g., end portion 102). (In configurations in which circuitry portion 100 is a mid-portion of PCB 92, rather than end portion 102, PCB 92 extends beyond circuitry portion 100, such as to provide electrical connection to additional elements, e.g., one or more electrodes and/or additional circuitry.) Electrical lead 90 is typically integrally fabricated as a track of elongate portion 91 of PCB 92 in connection with one or more of tracks 104 of PCB 92 that are part of circuitry 40, which obviates the need for a separate connection point between electrical lead 90 and circuitry 40.

For some of these applications, antenna 28 is coupled to circuitry 40 by being coupled to one side of circuitry portion 100 of PCB 92, such as shown in FIGS. 1A-B.

Optionally, elongate portion 91 of PCB 92 is shaped so as to define a plurality of protrusions 98 along elongate portion 91, which inhibit sutures 96 from sliding along elongate portion 91, such that the sutures 96 fix elongate portion 91 of PCB 92 securely to stent struts 190. Typically, protrusions 98 protrude laterally from elongate portion 91 of PCB 92 in a plane defined by PCB 92, either bidirectionally or in a single direction; optionally, some of protrusions 98 protrude bidirectionally and others of protrusions 98 protrude in a single direction, such as shown in the figures. Optionally, as labeled in the enlargement of FIG. 3A, an average distance D of lateral protrusion of protrusions 98 beyond non-protruding portions of elongate portion 91, in a single direction, equals 20%-100% of widths W of elongate portion 91 of PCB 92 at respective locations of the protrusions 98 along elongate portion 91, the average distance D and the widths W measured in the plane defined by PCB 92.

Reference is now made to FIGS. 3E and 3F. In these configurations, elongate portion 91 of PCB 92 is bifurcated, so as to define a main elongate portion 91A and two or more bifurcation elongate portions 91B. By way of example, exactly two bifurcation elongate portions 91B are shown in FIGS. 3E and 3F; in practice, elongate portion 91 may define more than two bifurcation elongate portions.

In some applications, respective electrodes 34, e.g., respective cathodes 54, are coupled to respective bifurcation elongate portions 91B at a respective plurality of angular locations around frame 30.

In some applications, such as shown in FIG. 3E, an electrical lead 90 integral with elongate portion 91 of PCB 92 is bifurcated, so as to define a main portion 90A and two or more bifurcation portions 90B integral with respective bifurcation elongate portions 91B of elongate portion 91 of PCB 92. For example, each of the bifurcation portions 90B of electrical lead 90 may be electrically coupled to a respective electrode 34, e.g., a respective cathode 54, in which case these electrodes are in electrical communication with each other. A separate electrical lead 90C may be provided integral with main elongate portion 91A of elongate portion 91 of PCB 92, in electrical connection with another electrode 34, e.g., an anode 56.

In other applications, such as shown in FIG. 3F, at least two electrical leads 90D and 90E integral with elongate portion 91 of PCB 92. Electrical leads 90D and 90E are partially integral with main elongate portion 91A of elongate portion 91 of PCB 92, and partially integral with respective bifurcation elongate portions 91B of elongate portion 91 of PCB 92. For example, each of electrical leads 90 may be electrically coupled to a respective electrode 34, e.g., a respective cathode 54, in which case these electrodes (e.g., cathodes) are in electrically isolated from each other, and separately electrically connected to circuitry 40. A separate electrical lead 90C may be provided integral with main elongate portion 91A of elongate portion 91 of PCB 92, in electrical connection with another electrode 34, e.g., an anode 56.

For some applications, such as in the configurations described with reference to FIGS. 3E and 3F, circuitry 40 is configured to apply a pacing signal using all of electrodes 34, e.g., all of cathodes 54. For other applications, such as in the configuration described with reference to FIG. 3F, circuitry 40 is configured to apply the pacing signal using fewer than all of electrodes 34, e.g., (a) fewer than all of cathodes 54, for example, using just a single one of cathodes 54, or two or more cathodes 54 of three or more provided cathodes 54, and/or fewer than all of anodes 56, for example, using just a single one of anodes 56, or two or more anodes 56 of three or more provided anodes 56. For some applications, circuitry 40 separately activates each of electrodes 34, e.g., cathodes 54 and/or anodes 56, at different times in different combinations, and, based on a determination of which of the electrodes 34 (e.g., cathodes 54, and/or anodes 56, in configurations which a plurality of anodes 56 are provided) provides the most effective pacing, uses this electrode 34, e.g., cathode 54 or anode 56, for future pacing.

For some applications, the determination regarding the most effective pacing is made based on the sensed ECG, as described hereinabove with reference to FIGS. 1A-B and 2, e.g., based on the combination of electrodes that results in the lowest ECG sensing threshold. Alternatively or additionally, for some applications, the determination regarding the most effective pacing is made by selecting the combination of electrodes that yields the lowest power, voltage, or current threshold sufficient for pacing, i.e., successful generation of a cardiac action potential.

In general, circuitry 40 is configured to apply the weakest pacing signal that yields an action potential in the heart. Circuitry 40 may be configured to induce pacing at a set voltage level or alternatively may be set to automatically determine the minimal voltage level of stimulation for a sufficient pacing.

For example, this determination regarding the most effective pacing may be made by circuitry 40 and/or by circuitry of an external control unit, such as external control unit 400, described hereinbelow with reference to FIG. 10. For some applications, this determination is performed (a) only once at the setup of the device immediately after implantation, (b) periodically, e.g., approximately once per day or once per week, and/or (c) before each pacing pulse is applied. An operator may or may not be involved in making the determination.

In some applications, this determination regarding the most effective pacing may be made by activating one or more of the upstream electrodes 34 as one or more anodes 56 (rather than as cathodes 54 as labeled in the drawings). Optionally, one or more upstream electrodes 34 are activated as one or more anodes 56, and one or more other upstream electrodes 34 are activated as one or more cathodes 54.

Reference is still made to FIGS. 3E-F. It is noted that for clarify of illustration, electrical lead 90 (including main portion 90A and bifurcation portions 90B), electrical lead 90C, electrical lead 90D, and/or electrical lead 90E are shown highly schematically in FIGS. 3E-F. In practice, these electrical leads are typically rectangular in cross section, e.g., having the exemplary dimensions provided hereinabove with reference to FIGS. 1A-B and 3A-D. In addition, these electrical leads may be disposed running alongside one another, such as shown in FIGS. 3E-F, and/or in layers with PCB 92 (configuration not shown), as is known in the PCB art.

Reference is made to FIGS. 3C and 3G. In the configurations shown in these figures, elongate portion 91 extends directly from circuitry portion 100 (e.g., end portion 102), and is typically integral with circuitry portion 100 (e.g., end portion 102). An end portion 103 of elongate portion 91 is bent in a curve over at least a portion of circuitry portion 100, so as to sandwich one or more stent struts 190 between circuitry portion 100 and elongate portion 91, such as shown in FIG. 3G (although not shown in FIG. 3C for the sake of clarity, stent struts 190 are in fact present in prosthetic aortic valve 20). The configurations shown in FIGS. 3C and 3G may optionally be implemented in combination with the other configurations shown herein. (In practice, the one or more stent struts 190 are typically sandwiched more snugly between circuitry portion 100 and elongate portion 91 than shown in FIG. 3G.)

Typically, circuitry portion 100 is disposed radially inward from stent struts 190, end portion 103 of elongate portion 91 is bent in a curve over at least a portion of circuitry portion 100, and the non-curved portion of elongate portion 91 that extends upstream from end portion 103 is disposed radially outward from stent struts 190.

For some applications, circuitry portion 100 is elongate, and end portion 103 of elongate portion 91 extends from a long lateral side 105 of circuitry portion 100, such as shown in FIG. 3C, or from a downstream end 107 of circuitry portion 100, such as shown in FIG. 3G. By contrast, if end portion 103 of elongate portion 91 were to instead extend from an upstream end of circuitry portion 100, elongate portion 91 might be more likely to be cut during crimping of frame 30. The circumferential width of stent cells 192 diminishes during crimping, while the height of stent cells 192 (in the axial direction) extends during crimping. If the rectangularly cross-sectioned elongate portion 91 were to cross the frame wall when extending from the upstream end of circuitry portion 100, elongate portion 91 might be squeezed between two struts during crimping, because the width of elongate portion 91 might be greater than the minimal distance between adjacent nodes or struts during crimping.

Reference is made to FIG. 3H. In this configuration, PCB 92 is shaped so as to define two or more circuitry portions 100 including a first circuitry portion 100A and a second circuitry portion 100B, for example, exactly two circuitry portions 100 (as shown) or three or more circuitry portions 100 (configuration not shown). One or more elongate circuitry-connecting portions 110 of PCB 92 connect the two or more circuitry portions 100. Typically, each of the one or more elongate circuitry-connecting portions 110 comprises one or more electrical leads that are integral with the respective elongate circuitry-connecting portion 110. For some applications, the one or more elongate circuitry-connecting portions 110 extend circumferentially around at least a portion of frame 30.

For some applications, the one or more elongate circuitry-connecting portions 110 are mechanically coupled to some of interconnected stent struts 190 of frame 30, and typically generally run along these stent struts (such that the one or more elongate circuitry-connecting portions 110 may have a zig-zag shape, for example).

Optionally, one of the two or more circuitry portions 100 (e.g., second circuitry portion 100B, as shown) is end portion 102 of PCB 92.

For some applications, circuitry 40 is distributed among the two or more circuitry portions 100, i.e., the two or more circuitry portions 100 comprises respective portions of electronic components of circuitry 40. This may allow the accommodation of circuitry 40 is case a single circuitry portion 100 does not have a sufficient surface area. For some applications, prosthetic aortic valve 20 comprises an energy storage module, e.g., comprising a battery, which is coupled to one of circuitry portions 100.

As used in the present application, including in the claims, "circuitry" means a combination of (a) one or more electronic components 106 and (b) one or more tracks 104 (also known as conductive traces) of a PCB electrically coupled to the one or more electrically components, typically by conductive pads of the PCB. The circuitry may or may not comprise a source of power. The one or more electronic components can be active components (e.g., semiconductor devices, such as integrated circuits, transistors, and/or active diodes); passive components (e.g., electrodes, capacitors, and/or passive diodes); and/or energy storage modules (e.g., comprising a battery). As used in the present application, including in the claims, tracks (also known as traces), electrical leads, wires, and cables are not considered to be electronic components.

Reference is again made to FIGS. 1A-B. The following configuration may be implemented alone or in combination with any of the other configurations described herein, including hereinabove with reference to FIGS. 3A-F and 3H. In this configuration, interconnected stent cells 192 of interconnected stent struts 190 of frame 30 include a first stent cell 170 shaped so as to define:
two peaks 172, consisting of an upstream peak 172A and a downstream peak 172B,
two lateral nodes 186, consisting of a left lateral node 186A and a right lateral node 186B,
two left stent struts 176, consisting of (a) an upstream left stent strut 176A joined with upstream peak 172A and left lateral node 186A, and (b) a downstream left stent strut 176B joined with downstream peak 172B and left lateral node 186A, and
two right stent struts 178, consisting of (a) an upstream right stent strut 178A joined with upstream peak 172A and right lateral node 186B, and (b) a downstream right stent strut 178B joined with downstream peak 172B and right lateral node 186B.

For example, first stent cell 170 may be located in a downstream half of frame 30, such as shown, e.g., first stent cell 170 may be a downstream-most stent cell (configuration not shown). Alternatively, first stent cell 170 may be located in an upstream half of frame 30 (configuration not shown in FIGS. 1A-B), e.g., first stent cell 170 may be an upstream-most stent cell (configuration not shown in FIGS. 1A-B).

In this configuration, prosthetic aortic valve 20 comprises an electronic component 150, which is disposed at or near one of peaks 172. For example, electronic component 150 may be part of circuitry 40 (such as shown), may comprise antenna 28 (also such as shown), may comprise an energy storage module, e.g., comprising a battery, or may comprise an electrode 34.

In this configuration, prosthetic aortic valve 20 further comprises coupling material 180, which is shaped so as to define:
a first strip 182A that is mechanically coupled to at least one of left stent struts 176,
a second strip 182B that is mechanically coupled to at least one of right stent struts 178, and
a junction 184, which couples together the first and the second strips 182A and 182B,
such that first and second strips 182A and 182B together couple electronic component 150 to frame 30 at or near (e.g., within 15 mm of) the one of peaks 172. Using first and second strips 182A and 182B in this arrangement to couple electronic component 150 to frame 30 typically helps stabilize electronic component 150 with respect to frame 30, both during expansion of frame 30 from its compressed elongated state, and during many cardiac cycles after implantation of frame 30.

By way of example and not limitation, in FIGS. 1A-B, first strip 182A is shown mechanically coupled to downstream left stent strut 176B, and second strip 182B is shown mechanically coupled to downstream right stent strut 178B, such that first and second strips 182A and 182B together couple electronic component 150 to frame 30 at or near downstream peak 172B. Alternatively, first strip 182A may be mechanically coupled to upstream left stent strut 176A, and second strip 182B may be mechanically coupled to upstream right stent strut 178A, such that first and second strips 182A and 182B together couple electronic component 150 to frame 30 at or near upstream peak 172A (configuration not shown).

Optionally, first and second strips 182A and 182B are integrally joined at junction 184, e.g., integrally formed from a single piece of material (such as shown); alternatively, first and second strips 182A and 182B comprise discrete pieces of material coupled together at junction 184 (configuration not shown). First strip 182A may be mechanically coupled to either surface of the at least one of left stent struts 176, and second strip 182B may be mechanically coupled to either surface of the at least one of right stent struts 178.

For some applications, first and second strips 182A and 182B together couple electronic component 150 to frame 30 at least partially outside the first stent cell at or near the one of peaks 172.

For some applications, first and second strips 182A and 182B are mechanically coupled to the at least one of left stent struts 176 and the at least one of right stent struts 178, respectively, by stitching.

For some applications, junction 184 of coupling material 180 is mechanically coupled to frame 30 at or near the one of peaks 172, such as by stitching.

For some applications, first strip 182A has length equal to at least 50% of a length of the at least one of left stent struts 176; for example, the length of first strip 182A may be greater than the length of the at least one of left stent struts 176. Alternatively or additionally, for some applications, second strip 182B has length equal to at least 50% of a length of the at least one of right stent struts 178; for example, the length of second strip 182B may be greater than the length of the at least one of right stent struts 178.

For some applications, first strip 182A is mechanically coupled to left lateral node 186A, such as by stitching. Alternatively or additionally, for some applications, second strip 182B is mechanically coupled to right lateral node 186B, such as by stitching.

For some applications, prosthetic aortic valve 20 further comprises an electrical lead, such as electrical lead 90, which is electrically coupled to electronic component 150, and first strip 182A is mechanically coupled to at least a portion of the electrical lead. For some of these applications, first strip 182A comprises electrical insulation, and first strip 182A electrically insulates the at least a portion of the electrical lead. For some applications, first strip 182A comprises an elongate portion of a PCB with which the electrical lead is integral, such as elongate portion 91 of PCB 92.

Figure 4:
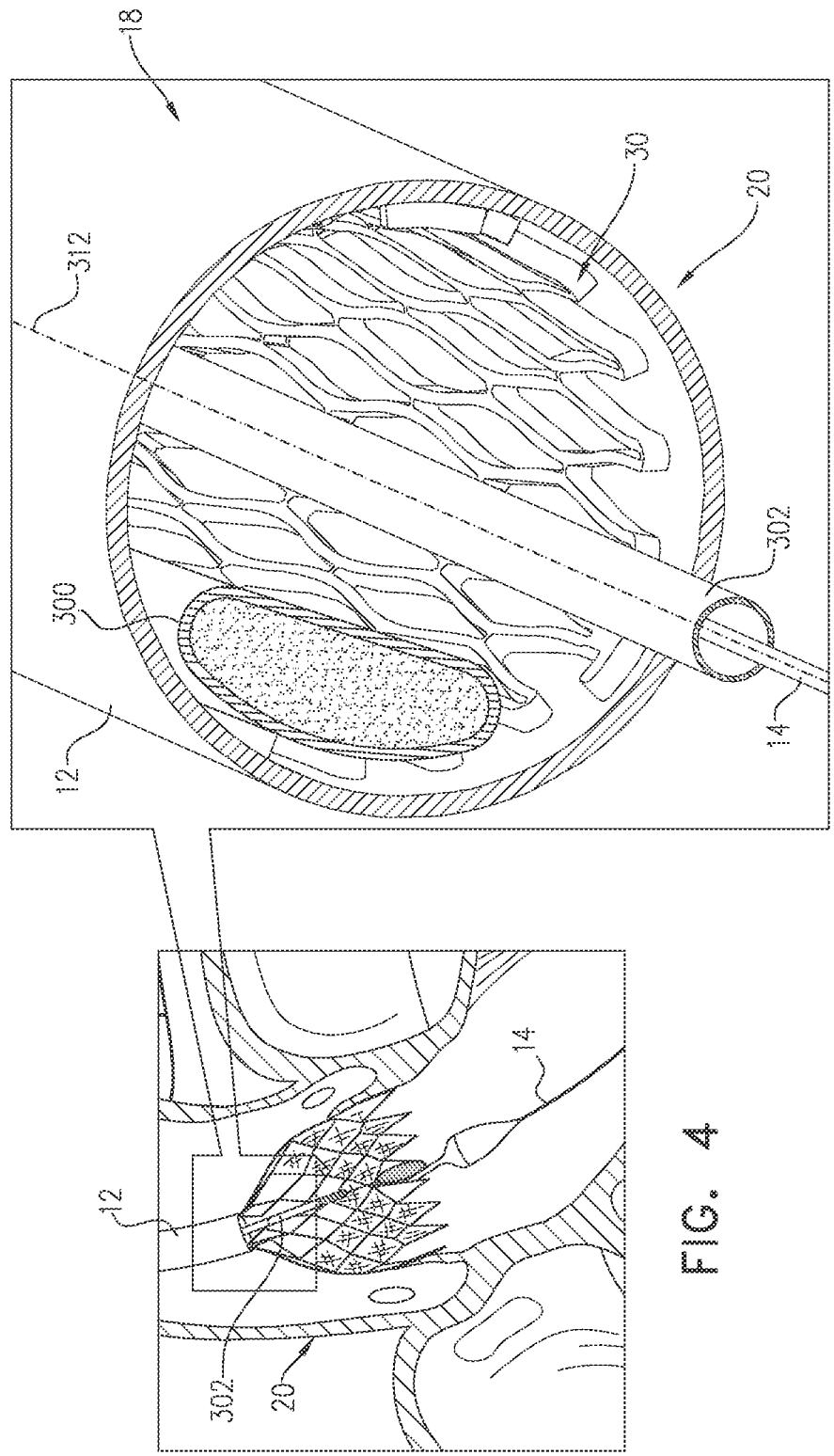
FIG. 4 is a schematic illustration of a portion of the prosthetic aortic valve of FIGS. 1A-B in a constrained delivery configuration within a delivery sheath, in accordance with an application of the present invention.

Reference is now made to FIG. 4, which is a schematic illustration of a portion of prosthetic aortic valve 20 in a constrained delivery configuration within delivery sheath 12, in accordance with an application of the present invention.

Figure 5A:
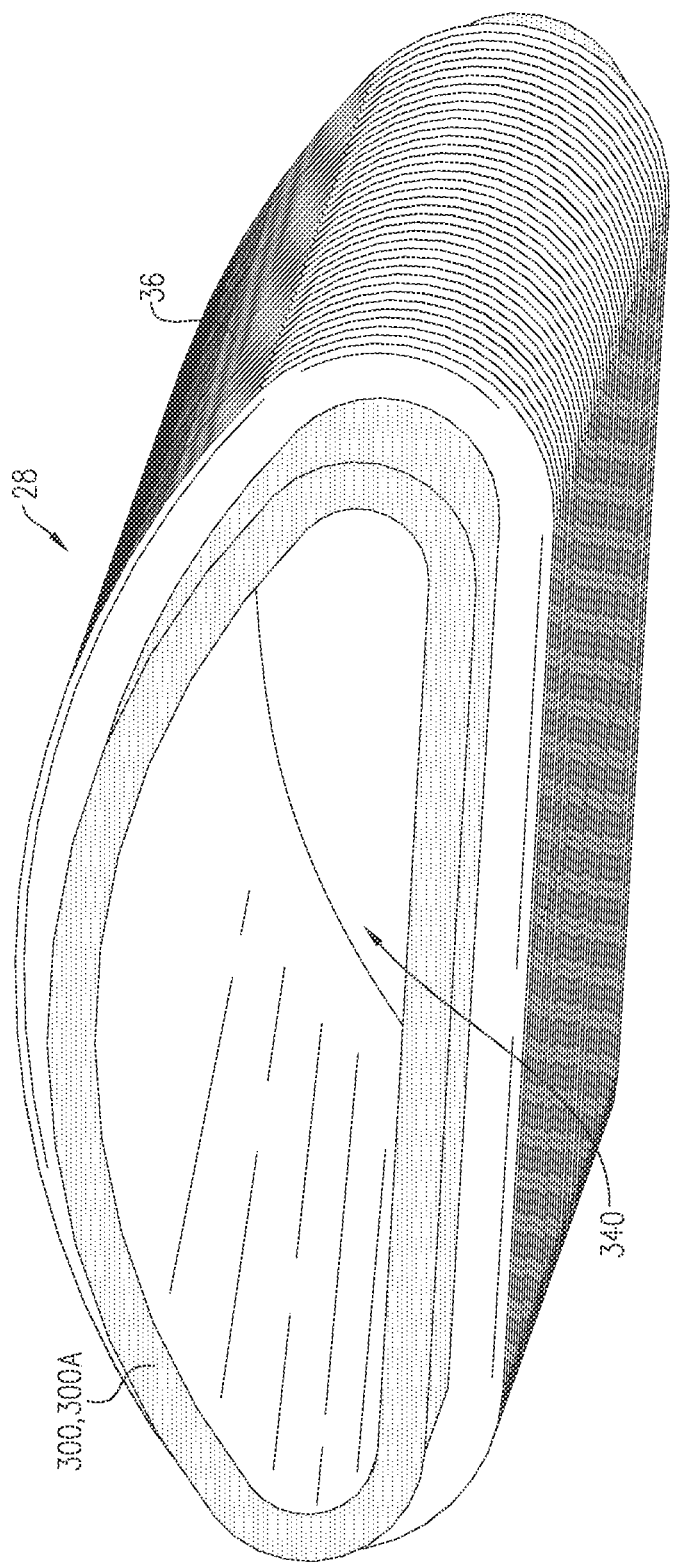
FIGS. 5A-B are schematic illustrations of a magnetic core of an antenna, in accordance with an application of the present invention.
Figure 5B:
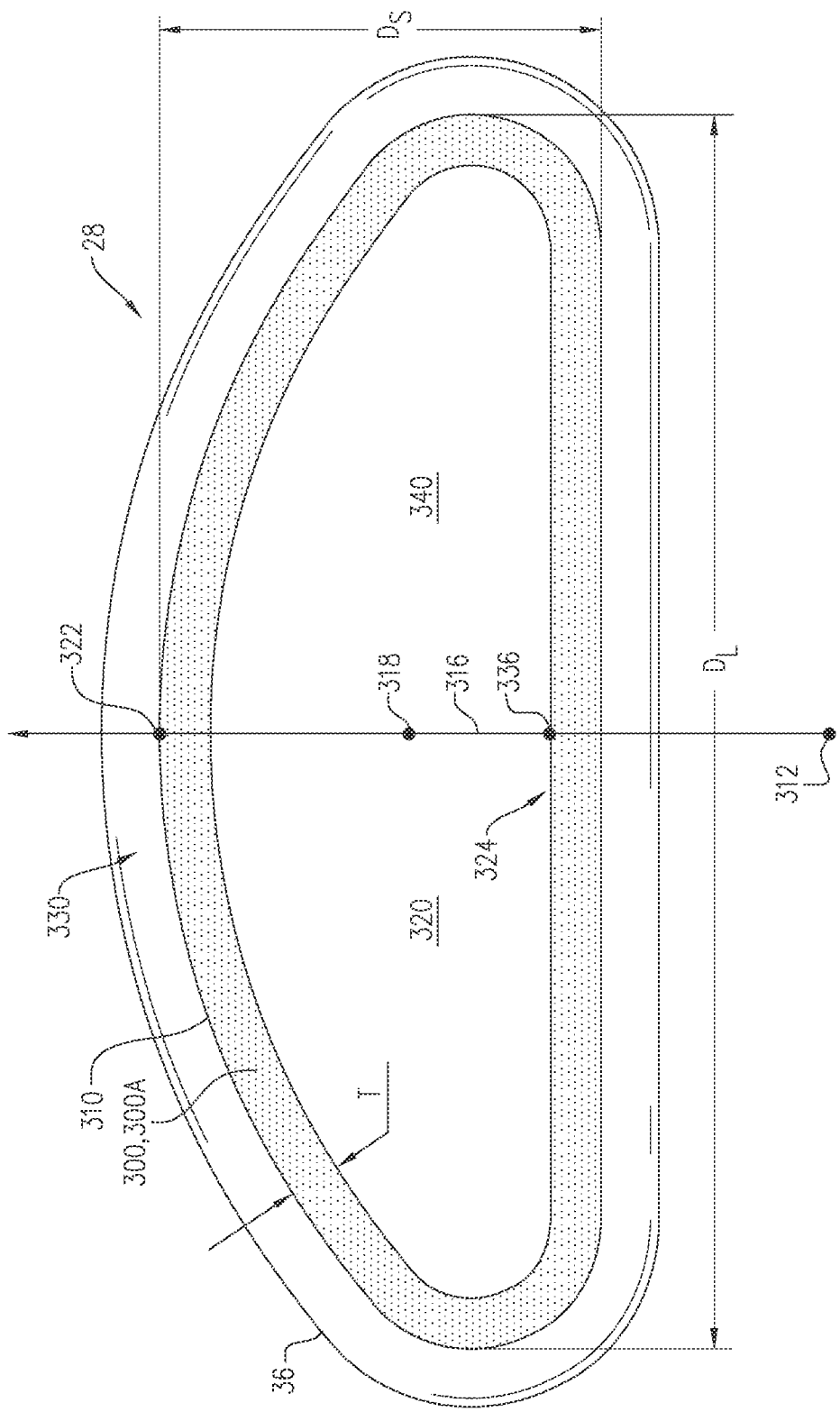

Reference is also made to FIGS. 5A-B, which are schematic illustrations of a magnetic core 300 of antenna 28, in accordance with an application of the present invention.

Figure 6A:
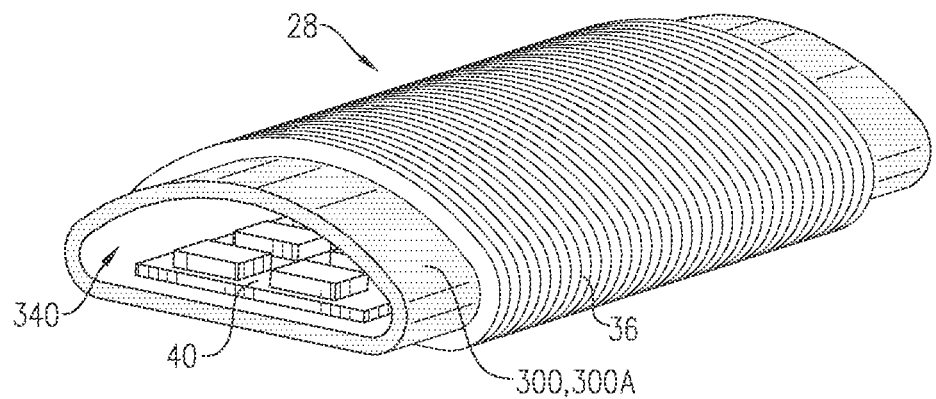
FIGS. 6A-B are schematic illustrations of another configuration of the magnetic core of the antenna of FIGS. 5A-B, in accordance with an application of the present invention.
Figure 6B:
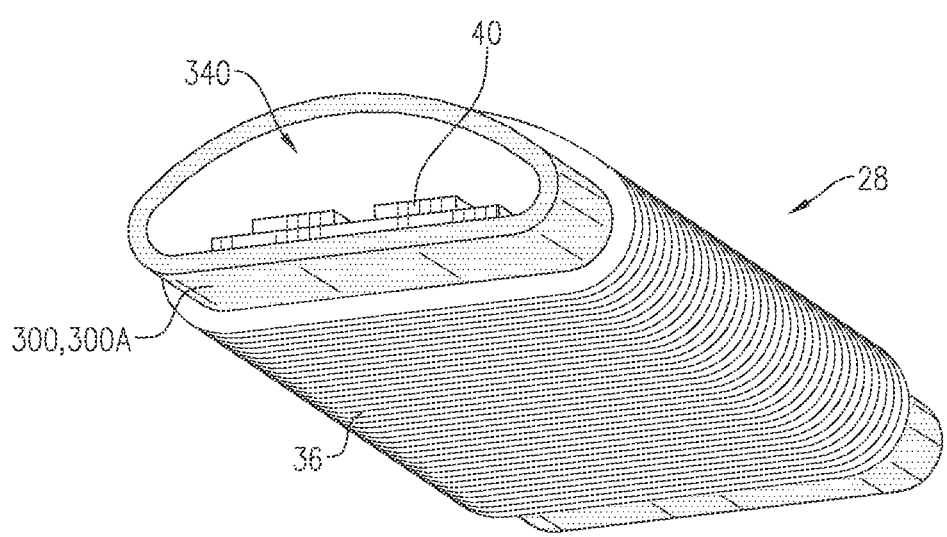

Reference is further made to FIGS. 6A-B, which are schematic illustrations of another configuration of magnetic core 300 of antenna 28, in accordance with an application of the present invention.

Figure 7:
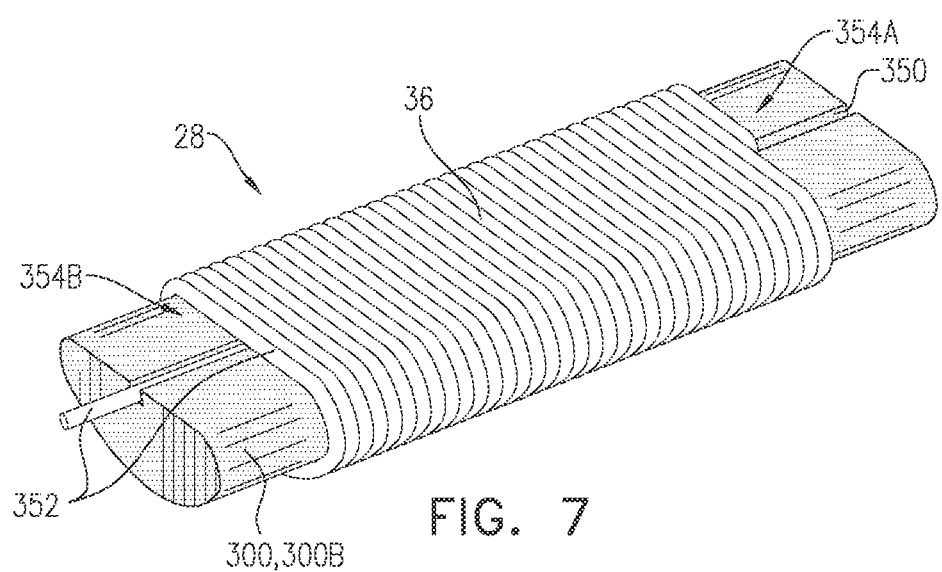
FIG. 7 is a schematic illustration of yet another configuration of the magnetic core of the antenna of FIGS. 5A-B, in accordance with an application of the present invention.

Reference is still further made to FIG. 7, which is a schematic illustration of yet another configuration of magnetic core 300 of antenna 28, in accordance with an application of the present invention.

In these configurations, the one or more prosthetic-valve coils 36 of antenna 28 are wound about magnetic core 300. Magnetic core 300 has a somewhat flattened, non-circular cross section, in order to provide good utilization of the space available on one side of frame 30 between frame 30 and an inner shaft 302 of delivery system 18 when prosthetic aortic valve 20 is in the constrained delivery configuration within delivery sheath 12, such as shown in FIG. 4.

Typically, antenna 28 is mechanically coupled to frame 30 downstream of prosthetic leaflets 32. As a result, magnetic core 300 is disposed at an axial location along prosthetic aortic valve 20 that is devoid of material of prosthetic leaflets 32, because the available space between frame 30 and inner shaft 302 is greater at this axial location than at other axial locations at which prosthetic leaflets 32 are disposed. (Typically, inner shaft 302 is shaped so as to define an internal guidewire channel, through which guidewire 14 passes, as is known in the catheter art.)

For some applications, as labeled in FIGS. 4 and 5B, at at least one location along a length of magnetic core 300, an outer perimeter 310 of magnetic core 300, in a plane perpendicular to a central longitudinal axis 312 of frame 30 when prosthetic aortic valve 20 is in the constrained delivery configuration, has:

- a shorter dimension $D_S$, which is measured along a ray 316 that (i) radiates radially outward from central longitudinal axis 312 and (ii) intersects a centroid 318 defined by a planar space 320 bound by outer perimeter 310, and
- a longer dimension $D_L$, which is measured perpendicular to the shorter dimension $D_S$ in the plane, and is at least 150% of the shorter dimension $D_S$.

(The location of central longitudinal axis 312 is shown schematically and not necessarily to scale in both FIG. 4 and FIG. 5B.)

For some applications, a radially-outward portion 330 of outer perimeter 310 of magnetic core 300, which includes a point 332 on outer perimeter 310 farthest from central longitudinal axis 312, is concavely curved with respect to central longitudinal axis 312. For some of these applications, radially-outward portion 330 of outer perimeter 310 of magnetic core 300 has:

- a greatest radius of curvature of at least 1 mm, no more than 5 mm, and/or 1-5 mm, e.g., at least 1.3 mm, no more than 4.5 mm, and/or 1.3-4.5, such as at least 1.5, no more than 3.5 mm, and/or 1.5-3.5, e.g., 2.2 mm.
- a greatest radius of curvature of at least 0.3 times the longer dimension $D_L$, no more than 1.6 times the longer dimension $D_L$, and/or 0.3-1.6 times the longer dimension $D_L$, e.g., 0.75-1 times the longer dimension $D_L$.

Alternatively or additionally, for some applications, a radially-inward portion 334 of outer perimeter 310, which includes a point 336 on outer perimeter 310 closest to central longitudinal axis 312, is flat, such as shown in the figures. Alternatively, for some applications, radially-inward portion 334 of outer perimeter 310, which includes one or more points on outer perimeter 310 closest to central longitudinal axis 312, is concavely curved with respect to central longitudinal axis 312 (configuration not shown); optionally, radially-inward portion 334 of outer perimeter 310 has a greatest radius of curvature that is less than a greatest radius of curvature of radially-outward portion 330 of outer perimeter 310.

For some applications, curved radially-outward portion 330 of outer perimeter 310 includes an arcuate portion of a circle. For example, the arcuate portion may have a measure of 45-180 degrees, e.g., 60-180 degrees, such as 60-120 degrees.

Reference is made to FIGS. 5A-B and 6A-B. For some applications, magnetic core 300 is a magnetic core 300, 300A, which is shaped so as to define a cavity 340. Circuitry 40 of prosthetic aortic valve 20 is disposed at least partially within cavity 340, such as entirely within cavity 340. Circuitry 40 is typically electrically coupled to the one or more prosthetic-valve coils 36. Optionally, circuitry 40 comprises circuitry portion 100 of PCB 92, such as described hereinabove with reference to FIG. 3E, and circuitry portion 100 of PCB 92 is disposed at least partially within cavity 340.

For some applications, magnetic core 300 has an average wall thickness T surrounding cavity 340 of 100-500 microns, and/or equal to at least 0.05 (e.g., at least 0.1) times the shorter dimension $D_S$, no more than 0.4 (e.g., no more than 0.3 or no more than 0.2) times the shorter dimension $D_S$, and/or 0.05-0.4 times the shorter dimension $D_S$.

For some applications, the longer dimension $D_L$ is at least 175% of the shorter dimension $D_S$, such as at least 200% of the shorter dimension $D_S$. For some applications, the longer dimension $D_L$ is no more than 400% of the shorter dimension $D_S$, such as no more than 350% of the shorter dimension $D_S$, e.g., equal to 300% of the shorter dimension $D_S$.

Reference is made to FIG. 7. For some applications, magnetic core 300 is a magnetic core 300, 300B, which is not shaped so as to define a cavity.

For some applications, an external surface of magnetic core 300 is shaped so as to define an axially-oriented groove 350. At least one of prosthetic-valve coils 36 comprises a wire 352, and a straight portion of wire 352 is disposed at least partially within axially-oriented groove 350, so as to pass from a first axial end 354A to a second axial end 354B of the at least one of prosthetic-valve coils 36. (In this context, "axially-oriented" means parallel to a central longitudinal axis of magnetic core 300, or defining an angle of less than 15 degrees with the central longitudinal axis.)

Groove 350 is illustrated in magnetic core 300, 300B by way of example and not limitation, and may be also be implemented in magnetic core 300, 300A, described with reference to FIGS. 5A-B and 6A-B.

Figure 8B:
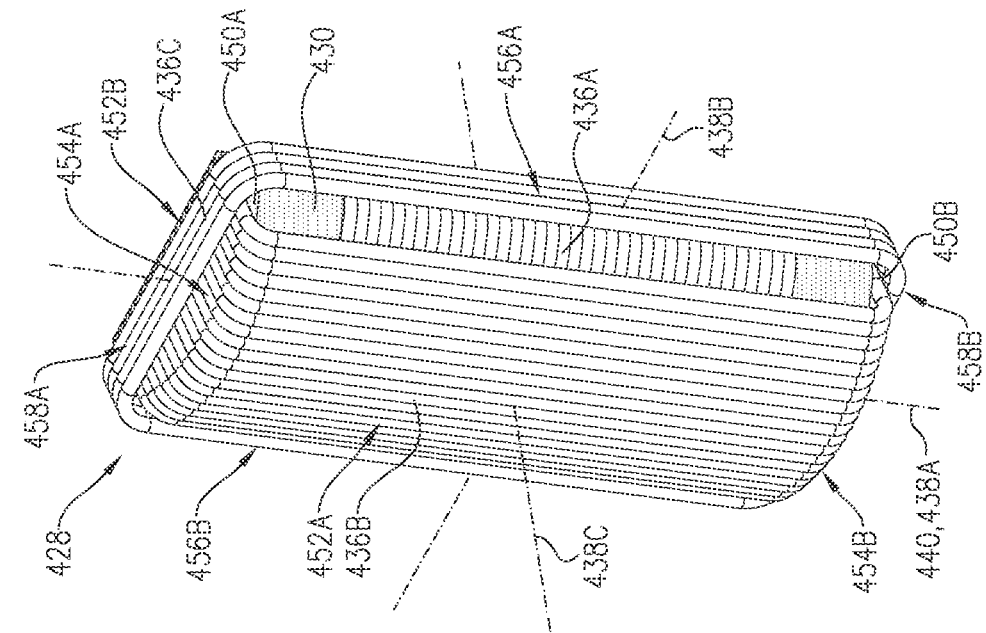
FIGS. 8A and 8B are schematic illustrations of another antenna, in accordance with respective applications of the present invention.
Figure 8A:
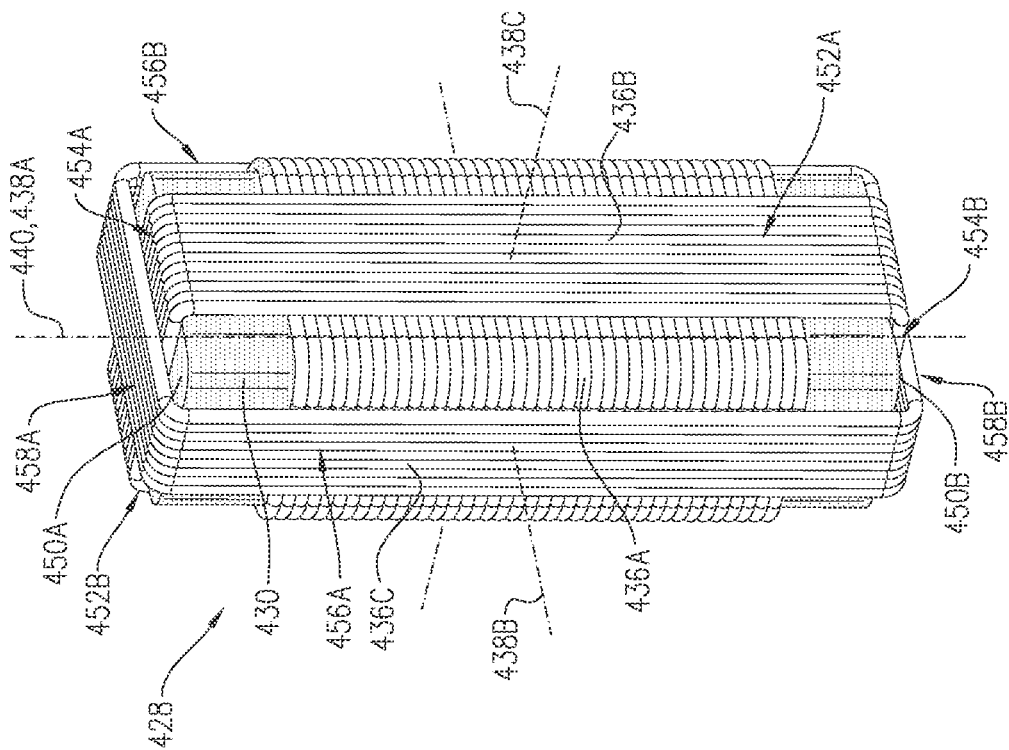

Reference is now made to FIGS. 8A and 8B, which are schematic illustrations of an antenna 428, in accordance with respective applications of the present invention. Antenna 428 may optionally be incorporated into prosthetic aortic valve 20 or another prosthetic aortic valve, or into another medical device configured to be placed and/or implanted in a body of a subject; alternatively, antenna 428 may implemented independently of any medical device.

Antenna 428 comprises an elongate core 430 and first, second, and third coils 436A, 436B, and 436C, which are wound around elongate core 430 such that:
- first coil 436A encircles a first-coil longitudinal axis 438A that coincides with a central longitudinal axis 440 of elongate core 430,
- second coil 436B encircles a second-coil longitudinal axis 438B that is perpendicular to first-coil longitudinal axis 438A, and
- third coil 436C encircles a third-coil longitudinal axis 438C that is perpendicular to first-coil longitudinal axis 438A and to second-coil longitudinal axis 438B.

For some applications, such as shown in FIG. 8B, antenna 428 implements the techniques of magnetic core 300, described hereinabove with reference to FIGS. 4, 5A-B, and/or 6A-B, while for other applications, antenna 428 does not implement these techniques, such as shown in FIG. 8A. In any event, first, second, and third coils 436A, 436B, and 436C typically are shaped at least in part based on the shape of the external surface of the core around which the coils are wound.

The longitudinal axes of the coils may or may not be centered within the respective coils.

Typically, first, second, and third coils 436A, 436B, and 436C are electrically isolated from one another and connected to circuitry 40 by separate electrical paths, such that circuitry 40 can separately utilize the coils as appropriate.

Providing three different directions of winding may reduce the dependence on proper orientation of antenna 428 with respect to the antenna of a transmitter/receiver, such as an external transmitter/receiver, e.g., as described hereinbelow with reference to FIG. 2 and/or FIG. 10. Circuitry, such as circuitry 40, may be configured to determine the most effective combination of one or more of the coils for use for transmission of energy and/or data, such as by separately using each of the coils. Alternatively or additionally, circuitry, such as circuitry 40, may be configured to determine an orientation of antenna 428 with respect to the antenna of a transmitter/receiver, such as an external transmitter/receiver, e.g., as described hereinbelow with reference to FIG. 2 and/or FIG. 10, based on the relative strengths of the signals in each of the coils. The circuitry may perform either of the above-mentioned determinations either during a preprocedural calibration procedure or during use of antenna 428.

For some applications, second and third coils 436B and 436C cross each other at one or both longitudinal ends 450A and 450B of elongate core 430. Although longitudinal ends 450A and 450B are shown as flat in FIGS. 8A and 8B, the ends may alternatively define curved surfaces, such as convex curved surfaces.

Second coil 436B typically has (a) two longer sides 452A and 452B, which may or may not have the same lengths as each other, and (b) two shorter sides 454A and 454B, which may or may not have the same lengths as each other. For some applications, the two longer sides 452A and 452B are parallel to central longitudinal axis 440 of elongate core 430, or define an angle of less than 10 degrees with respect to central longitudinal axis 440 of elongate core 430, such as less than 5 degrees.

For some applications, the two longer sides 452A and 452B cross first coil 436A at a plurality of first locations, and define angles of 75-90 degrees, such as 80-90 degrees, e.g., 85-90 degrees with first coil 436A at each of the plurality of first locations.

Similarly, third coil 436C typically has (a) two longer sides 456A and 456B, which may or may not have the same lengths as each other and/or as longer sides 452A and 452B, and (b) two shorter sides 458A and 458B, which may or may not have the same lengths as each other and/or as shorter sides 454A and 454B. For some applications, the two longer sides 456A and 456B are parallel to central longitudinal axis 440 of elongate core 430, or define an angle of less than 10 degrees with respect to central longitudinal axis 440 of elongate core 430, such as less than 5 degrees.

For some applications, the two longer sides 456A and 456B cross first coil 436A at a plurality of second locations, and define angles of 85-90 degrees with first coil 436A at each of the plurality of second locations.

Optionally, elongate core 430 of antenna 428 is shaped so as to define axially-oriented groove 350, described hereinabove with reference to FIG. 7.

Figure 9:
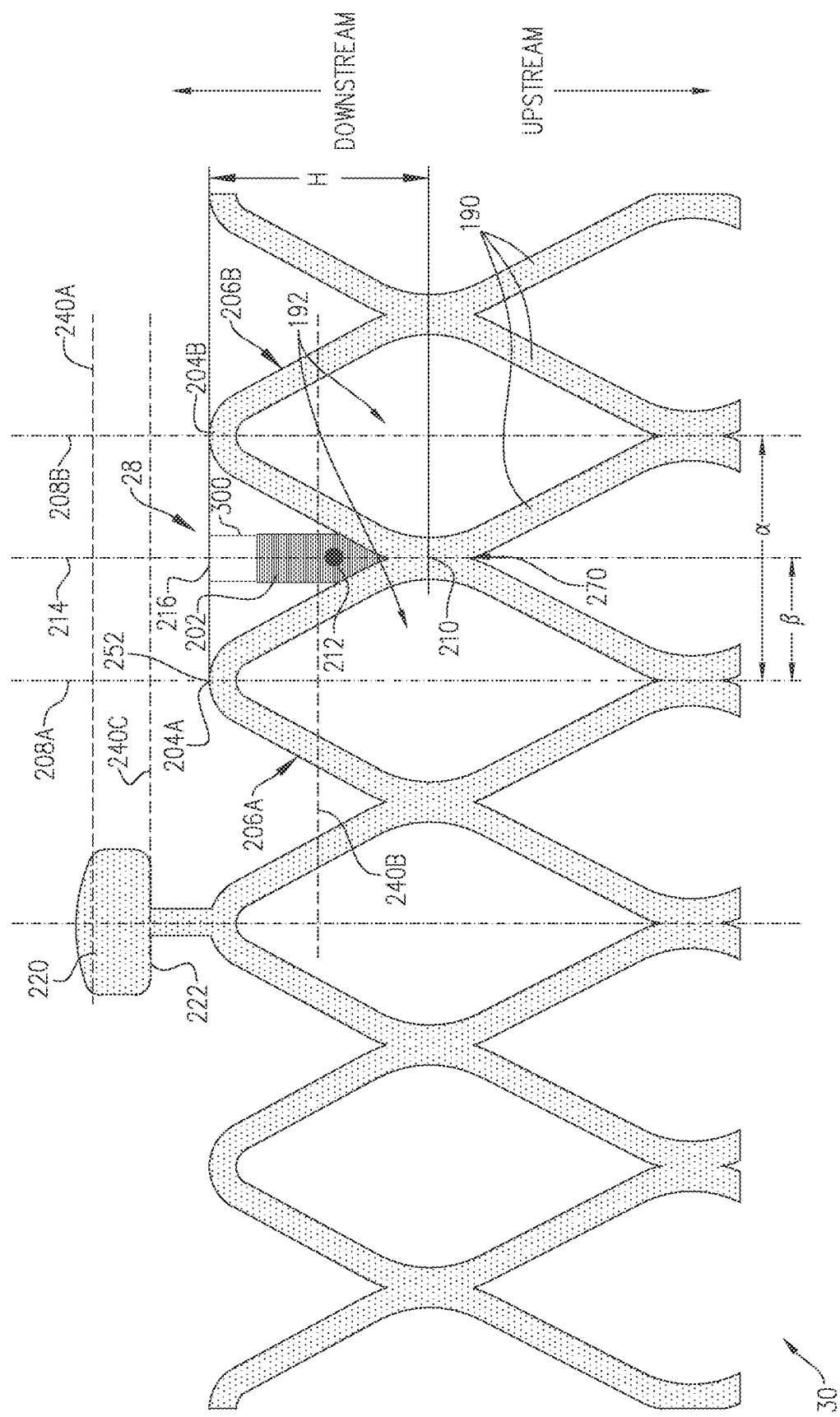
FIG. 9 is a schematic illustration of a frame of the prosthetic aortic valve of FIGS. 1A-B when the prosthetic aortic valve is in an expanded deployment configuration, in accordance with an application of the present invention.

Reference is now made to FIG. 9, which is a schematic illustration of frame 30 when prosthetic aortic valve 20 is in the expanded deployment configuration, in accordance with an application of the present invention. For clarity of illustration, the portion of frame 30 is shown laid flat; in practice, the frame is curved around central longitudinal axis 60 when prosthetic aortic valve 20 is in the expanded deployment configuration. In addition, although the description below and FIG. 9 relate to antenna 28, the same techniques are applicable to antenna 428.

For some applications, antenna 28 is approximately aligned with a downstream end of frame 30, between circumferentially adjacent first and second downstream-most stent cells 206A and 206B of interconnected stent cells 192. This location strikes a balance between the benefit of avoiding attenuation by the metal scaffold of frame 30 and the operational constraints of not interfering with the interface between one or more delivery-tool-coupling tabs 220 of frame 30 and delivery system 18. In an experiment conducted by one of the inventors, it was found that the relative attenuation when antenna 28 was disposed as shown in FIG. 9 was less than half of the relative attenuation when antenna 28 was disposed at the same axial location but instead within one of the cells.

As described above with reference to FIGS. 1A-B and FIG. 2, frame 30 defines central longitudinal axis 60 when prosthetic aortic valve 20 is in the expanded deployment configuration, and frame 30 comprises interconnected stent struts 190 arranged so as to define interconnected stent cells 192.

For some applications, first and second downstream peaks 204A and 204B respectively defined by circumferentially adjacent first and second downstream-most stent cells 206A and 206B of interconnected stent cells 192 are located at respective first and second peak angular locations 208A and 208B about central longitudinal axis 60 of frame 30. As used in the present application, including in the claims and Inventive Concepts, an "angular location" is a location on frame 30 at a particular location around central longitudinal axis 60, i.e., at a particular "o'clock" with respect to central longitudinal axis 60.

Antenna 28 is mechanically coupled to frame 30 such that:
- a centroid 212 of antenna 28 is at an antenna angular location 214 about central longitudinal axis 60, antenna angular location 214 between first and second peak angular locations 208A and 208B, and
- a downstream-most point 216 of antenna 28 is axially disposed between (i) 5 mm downstream of first and second downstream peaks 204A and 204B (schematically indicated by a line 240A) and (ii) 5 mm upstream of first and second downstream peaks 204A and 204B (schematically indicated by a line 240B).

Downstream-most point 216 of antenna 28 may be defined by a core of the antenna, such as magnetic core 300, such as shown in FIG. 9, or by one of the coils of the antenna, such as in the configuration of antenna 428, described hereinabove with reference to FIGS. 8A and 8B.

For some applications, antenna 28 is mechanically coupled to frame 30 such that downstream-most point 216 of antenna 28 is axially disposed between (i) 3 mm downstream of first and second downstream peaks 204A and 204B and (ii) 5 mm upstream of first and the second downstream peaks 204A and 204B (schematically indicated by a line 240B). For example, antenna 28 may be mechanically coupled to frame 30 such that downstream-most point 216 of antenna 28 is axially disposed at a same axial location as first and second downstream peaks 204A and 204B, such as shown in FIG. 9.

For some applications, antenna 28 is mechanically coupled to frame 30 such that downstream-most point 216 of antenna 28 is axially disposed between (i) 5 mm downstream of first and second downstream peaks 204A and 204B (schematically indicated by a line 240A) and (ii) 3 mm upstream of first and the second downstream peaks 204A and 204B. For some of these applications, antenna 28 is mechanically coupled to frame 30 such that downstream-most point 216 of antenna 28 is axially disposed between (i) 3 mm downstream of first and second downstream peaks 204A and 204B and (ii) 3 mm upstream of first and the second downstream peaks 204A and 204B.

For some applications, frame 30 further comprises one or more delivery-tool-coupling tabs 220, disposed downstream of stent cells 192, and shaped so as to define respective upstream-facing edges 222. The one or more delivery-tool-coupling tabs 220 are configured to removably couple frame 30, and thus prosthetic aortic valve 20, to delivery system 18, e.g., to a delivery shaft of delivery system 18.

For some of these applications, antenna 28 is mechanically coupled to frame 30 such that:
- centroid 212 of antenna 28 is at antenna angular location 214 about central longitudinal axis 60, antenna angular location 214 between first and second peak angular locations 208A and 208B, and
- downstream-most point 216 of antenna 28 is axially disposed between (i) an axial position of upstream-facing edges 222 of delivery-tool-coupling tabs 220 (schematically indicated by a line 240C) and (ii) 5 mm upstream of first and second downstream peaks 204A and 204B (schematically indicated by a line 240B) (it is noted that antenna 28 is typically circumferentially offset from delivery-tool-coupling tabs 220, such as shown).

For some applications, antenna 28 is mechanically coupled to frame 30 such that downstream-most point 216 of antenna 28 is axially disposed between (i) 2 mm upstream of upstream-facing edges 222 of delivery-tool-coupling tabs 220 and (ii) 5 mm upstream of first and second downstream peaks 204A and 204B (schematically indicated by a line 240B).

For some applications, antenna 28 is mechanically coupled to frame 30 such that downstream-most point 216 of antenna 28 is axially disposed between (i) 5 mm upstream of upstream-facing edges 222 of delivery-tool-coupling tabs 220 and (ii) 3 mm upstream of first and second downstream peaks 204A and 204B.

The locations of lines 240A, 240B, and 240C are shown in FIG. 9 by way of example and not limitation, and are based on exemplary approximate dimensions and shapes of interconnected stent struts 190 and interconnected stent cells 192.

For some applications, first and second downstream-most stent cells 206A and 206B are joined at cell junction 210, and antenna 28 is mechanically coupled to frame 30 at least in part by being mechanically coupled to cell junction 210. For some of these applications, an upstream-most point 270 of antenna 28 coincides with, or is no more than a distance upstream of, the cell junction, the distance equal to 30% of a length of antenna 28, such as 20% of the length of antenna 28, the distance and the length measured parallel to central longitudinal axis 60 of frame 30.

First and second peak angular locations 208A and 208B are angularly offset by a peak-to-peak angular offset α (alpha). First peak angular location 208A and antenna angular location 214 are angularly offset by a peak-to-antenna angular offset β (beta). For some applications, peak-to-antenna angular offset α (alpha) equals 25%-75% of peak-to-peak angular offset β (beta), e.g., 50%, as shown in FIG. 9.

For some applications, a width of antenna 28, measured in a peak-to-peak direction, equals 10%-60% of peak-to-peak angular offset α (alpha), e.g., 10%-30%, e.g., 15% of α (alpha).

A peak height H equals a distance between a downstream-most point 272 of first downstream peak 204A and cell junction 210, measured parallel to central longitudinal axis 60 of frame 30. For some applications, a length of antenna 28 equals 30%-150% of peak height H, such as 80-120%, e.g., 100%, of peak height H, the length and the peak height measured parallel to central longitudinal axis 60 of frame 30.

Figure 10:
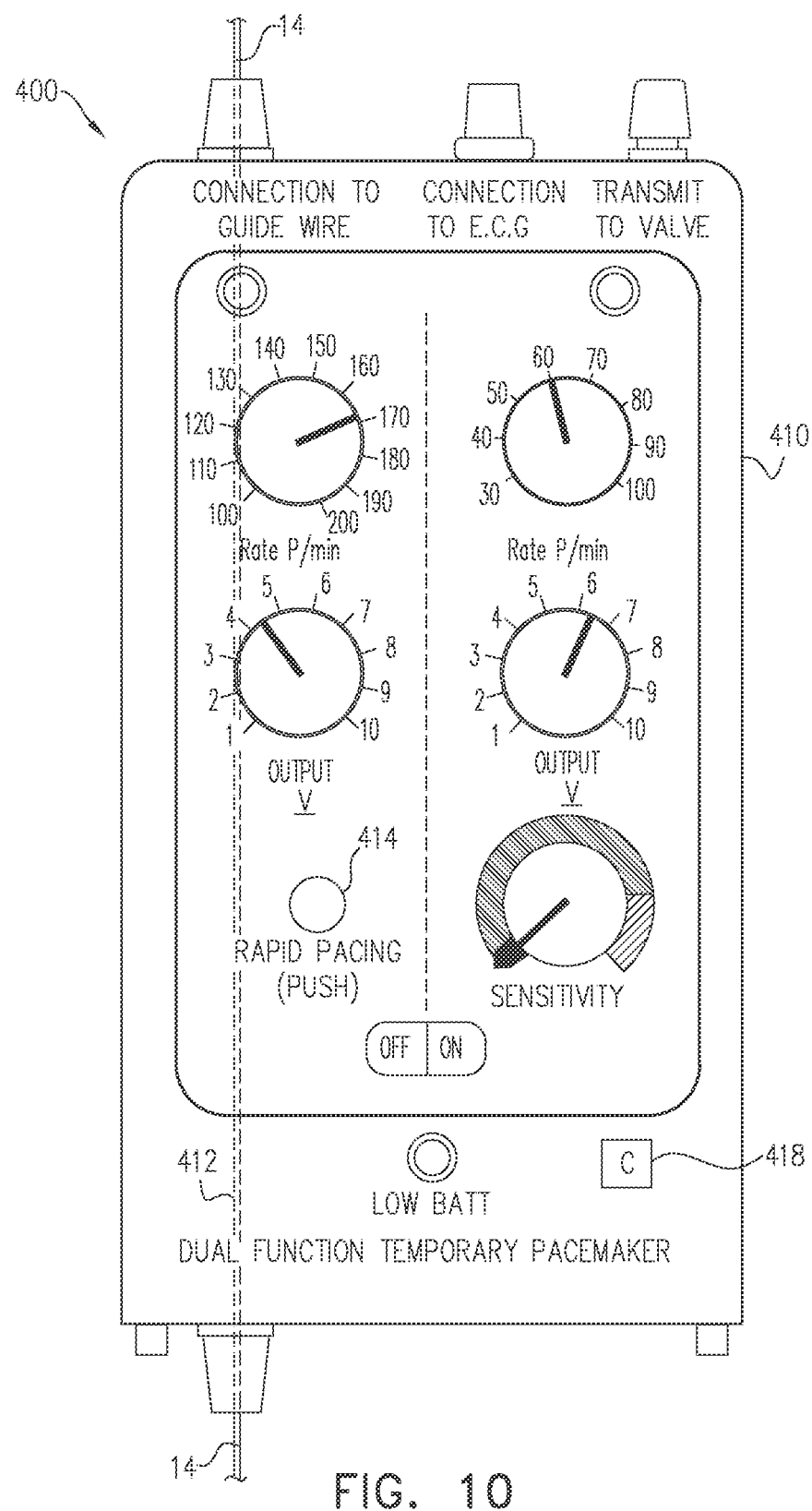
FIG. 10 is a schematic illustration of an external control unit of a valve prosthesis system comprising the prosthetic aortic valve of FIGS. 1A-B, in accordance with an application of the present invention.

Reference is now made to FIG. 10, which is a schematic illustration of an external control unit 400 of valve prosthesis system 10, in accordance with an application of the present invention. Prosthetic aortic valve 20 is configured to be delivered to a native aortic valve of a patient in a constrained delivery configuration within delivery sheath 12 using guidewire 14.

External control unit 400 is configured to be disposed outside a body of the patient, and comprises:
- a housing 410, which is shaped so as to define a guidewire-receiving channel 412;
- a rapid-pacing user control 414; and
- external-unit control circuitry 418.

Reference is again made to FIG. 2. Typically, an external system is provided that is configured to be disposed outside a body of the patient. The external system comprises an external control unit, such as external control unit 400. The external system further comprises an external transmitter and/or receiver, which comprises an external coil 420, which is highly schematically illustrated in FIG. 2. For example, external coil 420 may be configured to be placed around the subject's chest, such as schematically shown in FIG. 2, or placed against the chest without surrounding the chest, such as against the sternum (configuration not shown). The external transmitter and/or receiver is configured to drive external coil 420 to wirelessly transfer energy to at least one of the one or more prosthetic-valve coils 36 by inductive coupling. For example, the external transmitter may transmit RF energy at a frequency of 2-300 MHz, e.g., 6.78 MHz.

Reference is again made to FIG. 10. As described hereinabove with reference to FIGS. 1A-B and 2, for some applications, circuitry 40 is configured to apply both regular pacing and rapid pacing. For example, the rapid pacing may be applied during an invasive structural heart procedure, such as an implantation procedure, such as a TAVR-in-TAVR procedure in which the first TAVR comprises prosthetic aortic valve 20, and a portion of the regular pacing may be applied temporarily while the patient is hospitalized after implantation of prosthetic aortic valve 20. External control unit 400 may be provided for controlling both the regular pacing and the rapid pacing. (When the patient is discharged from the hospital, an external control unit is typically provided having fewer or no user controls accessible by the patient.) Because the user or healthcare works may have access to external control unit 400, it is desirable to prevent accidental activation of rapid pacing after completion of the implantation procedure.

To this end, for some applications, external-unit control circuitry 418 is configured to:
- drive the energy-transmission coil to wirelessly transfer energy to at least one of the one or more prosthetic-valve coils 36 by inductive coupling, such as for powering regular pacing, and
- only upon activation of rapid-pacing user control 414 and when guidewire 14 is disposed within guidewire-receiving channel 412 of housing 410, drive prosthetic aortic valve 20 to apply rapid pacing using cathode 54 and anode 56.

To this end, external control unit 400 comprises a sensor, configured to sense whether guidewire 14 is disposed within guidewire-receiving channel 412 of housing 410.

This feature may serve as a safety feature, which restricts application of the rapid pacing to a transcatheter or surgical cardiovascular operation by a certified medical interventionalist.

The techniques described herein for prosthetic aortic valve 20 may be alternatively used, mutatis mutandis, for non-aortic prosthetic valves, such as prosthetic mitral or tricuspid valves.

In an embodiment, techniques and apparatus described in one or more of the following patents and/or applications, which are assigned to the assignee of the present application and are incorporated herein by reference, are combined with techniques and apparatus described herein:
- U.S. Pat. No. 10,543,083 to Gross
- European Patent Application Publication EP 3508113 A1 to Gross
- U.S. Pat. No. 10,835,750 to Gross
- U.S. Pat. No. 11,013,597 to Gross
- PCT Publication WO 2021/140507 to Gross
- PCT Publication WO 2021/224904 to Gross
- U.S. Pat. No. 11,065,451 to Gross
- U.S. Pat. No. 11,291,844 to Gross
- PCT Publication WO 2022/149130 to Gross It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A prosthetic aortic valve, which is configured to be delivered to a native aortic valve of a patient in a constrained delivery configuration, and which comprises:
- a frame, which defines a central longitudinal axis when the prosthetic aortic valve is in the constrained delivery configuration, and which comprises interconnected stent struts arranged so as to define interconnected stent cells;
- a plurality of prosthetic leaflets coupled to the frame so as to allow blood flow in a downstream direction and inhibit blood flow in an upstream direction when the prosthetic aortic valve is in an expanded deployment configuration;
- circuitry, which is mechanically coupled to the frame;
- an electrode, which is mechanically coupled to the frame;
- a printed circuit board (PCB), which is shaped so as to define (a) an elongate portion and (b) a circuitry portion distinct from the elongate portion, wherein the circuitry is coupled to the circuitry portion of the PCB; and an electrical lead, which electrically couples the electrode to the circuitry, and which is integral with the elongate portion of the PCB, and wherein the elongate portion of the PCB is mechanically coupled to some of the interconnected stent struts of the frame.

2. The prosthetic aortic valve according to claim 1, wherein the elongate portion of the PCB has an undulating shape that generally runs along the interconnected stent struts.

3. The prosthetic aortic valve according to claim 1, wherein the circuitry is mechanically coupled to the frame downstream of the prosthetic leaflets, and the electrode is mechanically coupled to the frame upstream of the prosthetic leaflets.

4. The prosthetic aortic valve according to claim 1, wherein the stent struts and the elongate portion of the PCB are rectangular in cross section taken perpendicular to respective longitudinal axes of the stent struts and the elongate portion.

5. The prosthetic aortic valve according to claim 1, wherein a ratio of a thickness of the stent struts to a thickness of the electrical lead is 5-15.

6. The prosthetic aortic valve according to claim 1, wherein a ratio of a thickness of the stent struts to a thickness of the elongate portion of the PCB is 2-5.

7. The prosthetic aortic valve according to claim 1, wherein the circuitry comprises (a) tracks of the PCB, (b) conductive pads of the PCB, and (c) electronic components coupled to the PCB.

8. The prosthetic aortic valve according to claim 7,
wherein the circuitry portion of the PCB is a first circuitry portion of the PCB, and
wherein the PCB is shaped so as to define:
a second circuitry portion, comprising one or more electronic components, and
an elongate circuitry-connecting portion, which connects the first circuitry portion to the second circuitry portion, and which comprises an electrical lead that is integral with the elongate circuitry-connecting portion.

9. The prosthetic aortic valve according to claim 8, wherein the elongate circuitry-connecting portion is oriented circumferentially around a circumferential portion of the frame.

10. The prosthetic aortic valve according to claim 8, wherein the one or more electronic components of the second circuitry portion comprise an energy storage module.

11. The prosthetic aortic valve according to claim 7, wherein the circuitry portion of the PCB is an end portion of the PCB.

12. The prosthetic aortic valve according to claim 7, wherein the elongate portion of the PCB extends directly from the circuitry portion of the PCB.

13. The prosthetic aortic valve according to claim 7, wherein the elongate portion of the PCB is integral with the circuitry portion the PCB.

14. The prosthetic aortic valve according to claim 13, wherein the electrical lead is fabricated as a track of the elongate portion of the PCB in connection with one or more of the tracks of the PCB that are part of the circuitry.

15. The prosthetic aortic valve according to claim 1,
wherein the elongate portion of the PCB is mechanically coupled to some of the interconnected stent struts of the frame by suturing using sutures, and
wherein the elongate portion of the PCB is shaped so as to define a plurality of protrusions along the elongate portion, which inhibit the sutures from sliding along the elongate portion, such that the sutures fix the elongate portion of the PCB securely to the stent struts.

16. A prosthetic aortic valve, which is configured to be delivered to a native aortic valve of a patient in a constrained delivery configuration, and which comprises:
a frame, which defines a central longitudinal axis when the prosthetic aortic valve is in the constrained delivery configuration, and which comprises interconnected stent struts arranged so as to define interconnected stent cells;
a plurality of prosthetic leaflets coupled to the frame so as to allow blood flow in a downstream direction and inhibit blood flow in an upstream direction when the prosthetic aortic valve is in an expanded deployment configuration;
circuitry, which is mechanically coupled to the frame;
an electrode, which is mechanically coupled to the frame;
a printed circuit board (PCB), which is shaped so as to define an elongate portion; and
an electrical lead, which electrically couples the electrode to the circuitry, and which is integral with the elongate portion of the PCB, and
wherein the elongate portion of the PCB is mechanically coupled to some of the interconnected stent struts of the frame,
wherein the elongate portion of the PCB is mechanically coupled to some of the interconnected stent struts of the frame by suturing using sutures,
wherein the elongate portion of the PCB is shaped so as to define a plurality of protrusions along the elongate portion, which inhibit the sutures from sliding along the elongate portion, such that the sutures fix the elongate portion of the PCB securely to the stent struts, and
wherein the protrusions protrude laterally from the elongate portion of the PCB in a plane defined by the PCB.

17. The prosthetic aortic valve according to claim 16, wherein an average distance of lateral protrusion of the protrusions beyond non-protruding portions of the elongate portion, in a single direction, equals 20%-100% of widths of the elongate portion of the PCB at respective locations of the protrusions along the elongate portion, the average distance and the widths measured in the plane defined by the PCB.

18. The prosthetic aortic valve according to claim 1, wherein the elongate portion of the PCB is bifurcated, so as to define a main elongate portion and two or more bifurcation elongate portions.

19. The prosthetic aortic valve according to claim 18, wherein the electrical lead is bifurcated, so as to define a main portion and two or more bifurcation portions integral with respective bifurcation elongate portions of the elongate portion of the PCB.

20. The prosthetic aortic valve according to claim 18, wherein the electrical lead is one of a plurality of electrical leads, which are partially integral with the main elongate portion of the elongate portion of the PCB, and partially integral with respective bifurcation elongate portions of the elongate portion of the PCB.

21. The prosthetic aortic valve according to claim 1, wherein the electrical lead is encased in the elongate portion of the PCB.

22. The prosthetic aortic valve according to claim 1, wherein the electrode is mechanically coupled to the frame at or near an upstream peak of one of upstream-most ones of the stent cells.

* * * * *